United States Patent [19]
Gustilo et al.

[11] Patent Number: 5,925,049
[45] Date of Patent: Jul. 20, 1999

[54] DEVICE AND METHOD FOR DISTAL FEMUR CUTTING AND PROSTHESIS MEASURING

[75] Inventors: Ramon B. Gustilo, Eden Prairie; William D. Lew, Mendota Heights, both of Minn.

[73] Assignee: Midwest Orthopedic Research Foundation, Minneapolis, Mich.

[21] Appl. No.: 08/918,924

[22] Filed: Aug. 26, 1997

Related U.S. Application Data

[63] Continuation of application No. 08/606,270, Feb. 23, 1996, abandoned.

[51] Int. Cl.⁶ .................................................. A61B 17/56
[52] U.S. Cl. .............................................. 606/82; 606/88
[58] Field of Search .................................. 606/88, 89, 87, 606/86, 96, 79, 80, 82, 102

[56] References Cited

U.S. PATENT DOCUMENTS

| | | |
|---|---|---|
| 4,457,307 | 7/1984 | Stillwell . |
| 4,474,177 | 10/1984 | Whiteside . |
| 4,501,266 | 2/1985 | McDaniel . |
| 4,566,448 | 1/1986 | Rohr, Jr. . |
| 4,567,885 | 2/1986 | Androphy . |
| 4,646,729 | 3/1987 | Kenna et al. . |
| 4,653,488 | 3/1987 | Kenna . |
| 4,703,751 | 11/1987 | Pohl . |
| 4,718,413 | 1/1988 | Johnson . |
| 4,722,330 | 2/1988 | Russell et al. . |
| 4,759,350 | 7/1988 | Dunn et al. . |
| 4,773,407 | 9/1988 | Petersen . |
| 4,825,857 | 5/1989 | Kenna . |
| 4,892,093 | 1/1990 | Zarnowski . |
| 4,892,546 | 1/1990 | Kotz et al. . |
| 4,907,578 | 3/1990 | Petersen . |
| 4,926,847 | 5/1990 | Luckman . |
| 4,935,023 | 6/1990 | Whiteside et al. . |
| 4,938,762 | 7/1990 | Wehrli . |
| 5,002,547 | 3/1991 | Poggie et al. . |
| 5,037,423 | 8/1991 | Kenna . |
| 5,098,436 | 3/1992 | Ferrante et al. . |
| 5,122,144 | 6/1992 | Bert et al. . |
| 5,129,909 | 7/1992 | Sutherland . |
| 5,197,488 | 3/1993 | Kovacevic . |
| 5,213,112 | 5/1993 | Niwa et al. . |
| 5,228,459 | 7/1993 | Caspari et al. . |
| 5,234,433 | 8/1993 | Bert et al. . |
| 5,250,050 | 10/1993 | Poggie et al. . |
| 5,312,411 | 5/1994 | Steele et al. . |
| 5,342,367 | 8/1994 | Ferrante et al. . |
| 5,364,401 | 11/1994 | Ferrante et al. . |
| 5,364,402 | 11/1994 | Mumme et al. . |
| 5,417,694 | 5/1995 | Marik et al. .............................. 606/88 |
| 5,445,642 | 8/1995 | McNulty et al. ......................... 606/88 |
| 5,486,178 | 1/1996 | Hodge ...................................... 606/82 |

FOREIGN PATENT DOCUMENTS

| | | |
|---|---|---|
| 380451 | 8/1990 | European Pat. Off. . |
| 466659 | 1/1992 | European Pat. Off. . |
| 538153 | 4/1993 | European Pat. Off. . |

*Primary Examiner*—Guy V. Tucker
*Attorney, Agent, or Firm*—Patterson & Keough, P.A.

[57] ABSTRACT

The invention provides surgical resection instruments, and methods of use, for facilitating accurately cut surfaces for the placement of femoral prosthesis components. The posterior condyles and anterior femoral cortex provide reference points for measurement and cuts of the femur with these instruments. One embodiment of the femoral resection instrument provides for precise anterior cuts of the femur appropriate for one of several sizes of prosthesis components without the need for separate cutting guides. Another embodiment provides for shifting the cutting location of both the posterior and anterior cuts by a portion of the distance between sizes of the prosthesis components while maintaining the reference position relative to the posterior part of the condyles and corresponding intercondylar notch. A third embodiment has an adjustable paddle so that the femoral resection instrument can be adjusted to the correct orientation when the femoral condyles are worn unequally. These various features may be combined, as desired. The invention includes related methods.

10 Claims, 16 Drawing Sheets

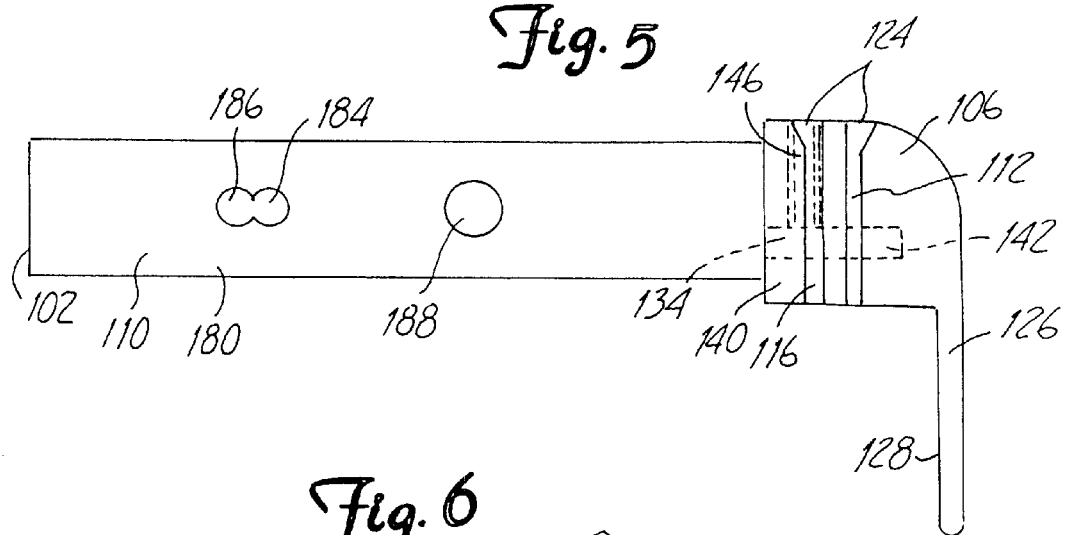
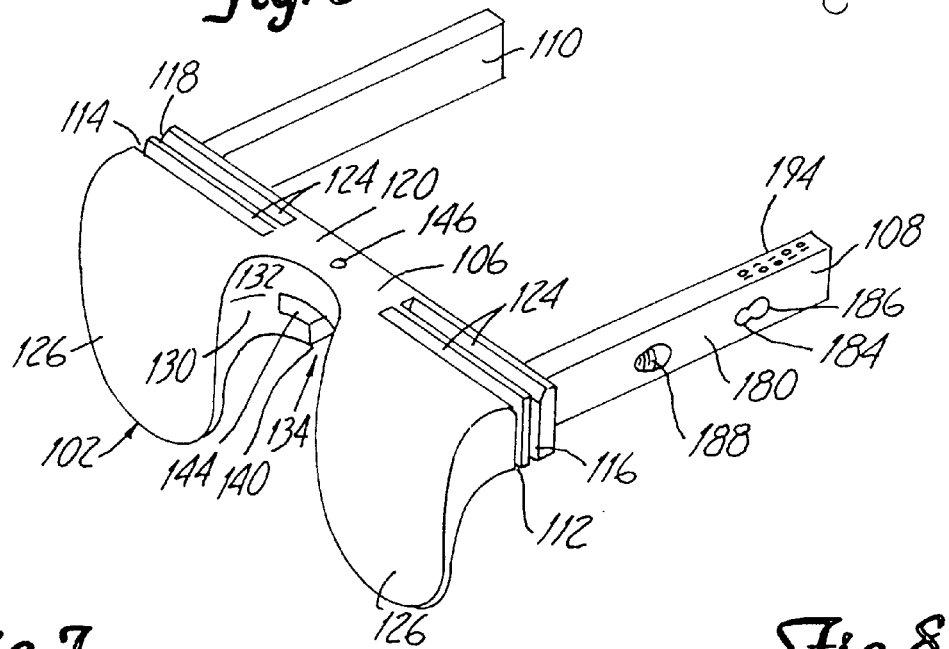
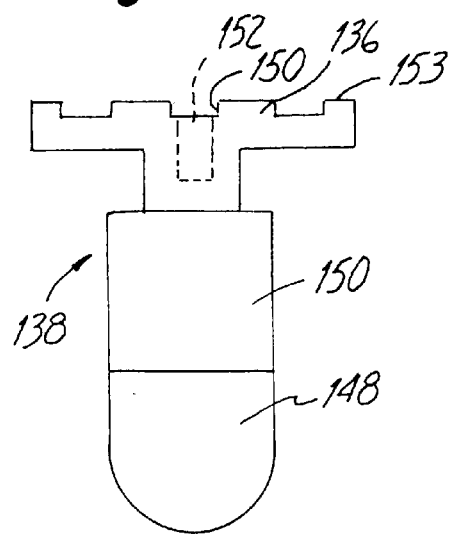
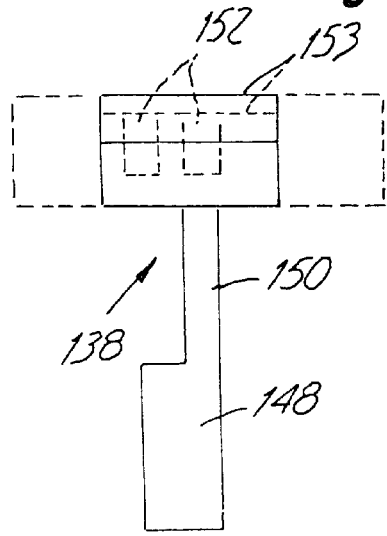

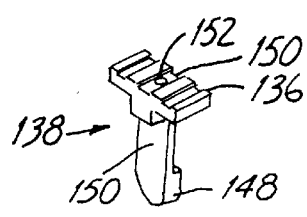
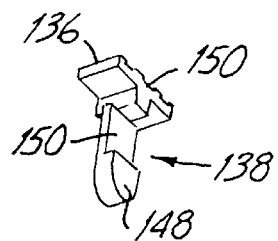
Fig. 9    Fig. 10
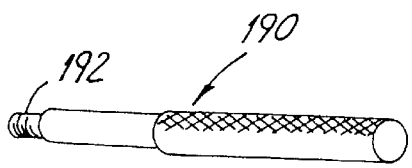
Fig. 11
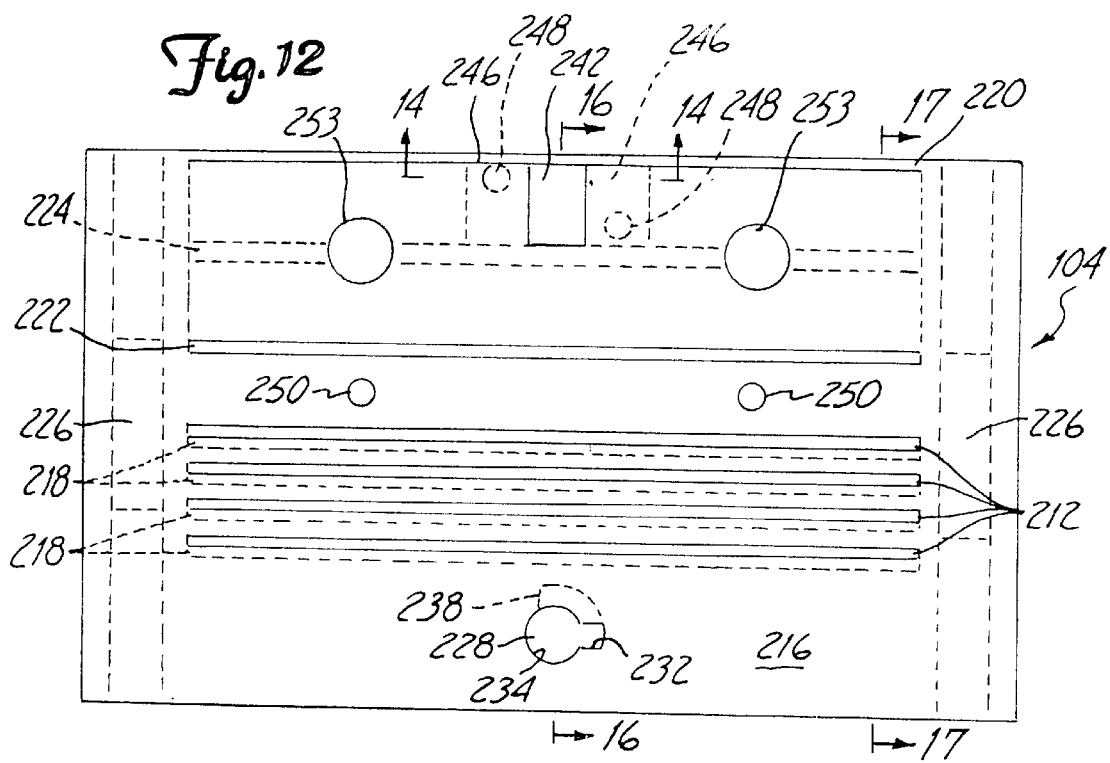
Fig. 12

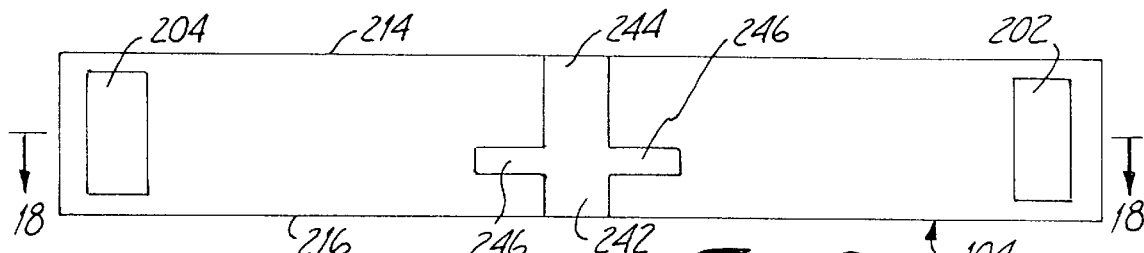
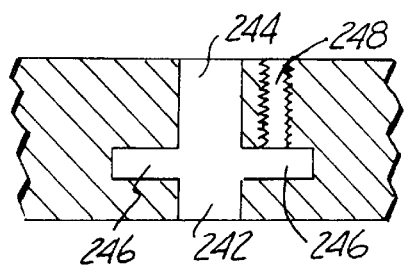
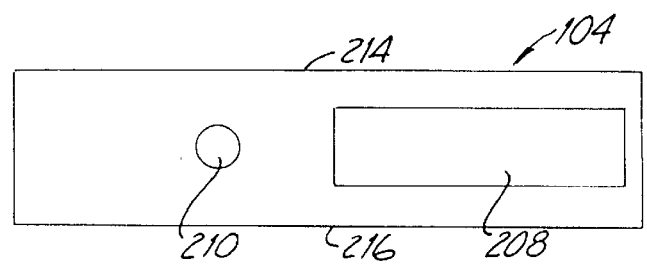
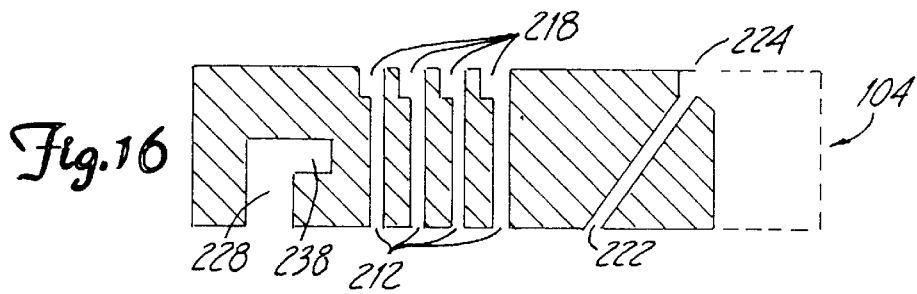
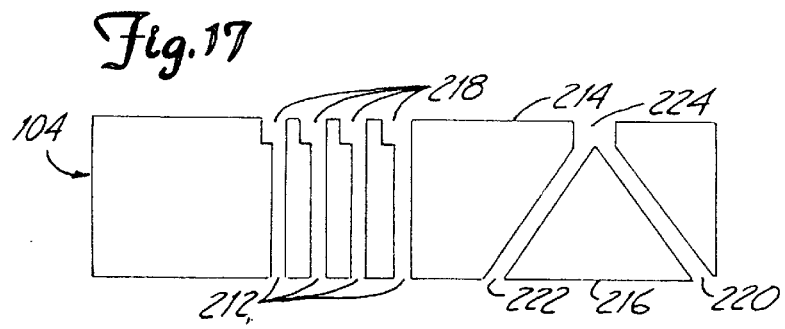

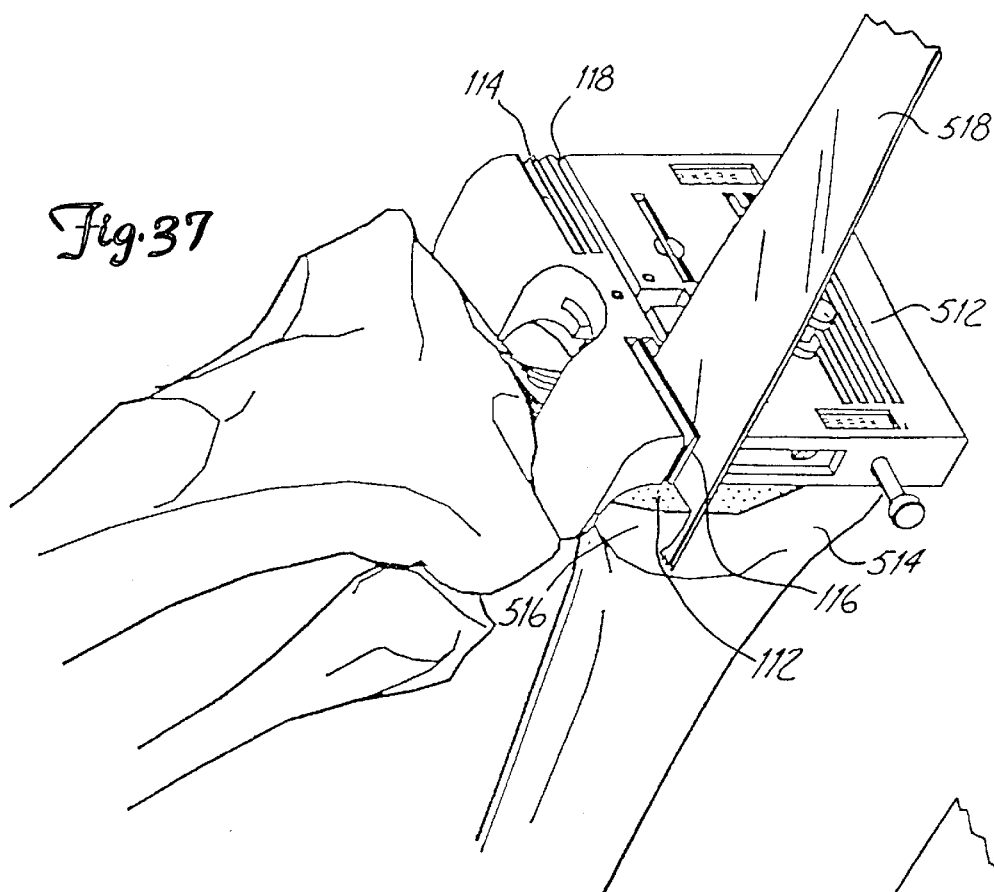
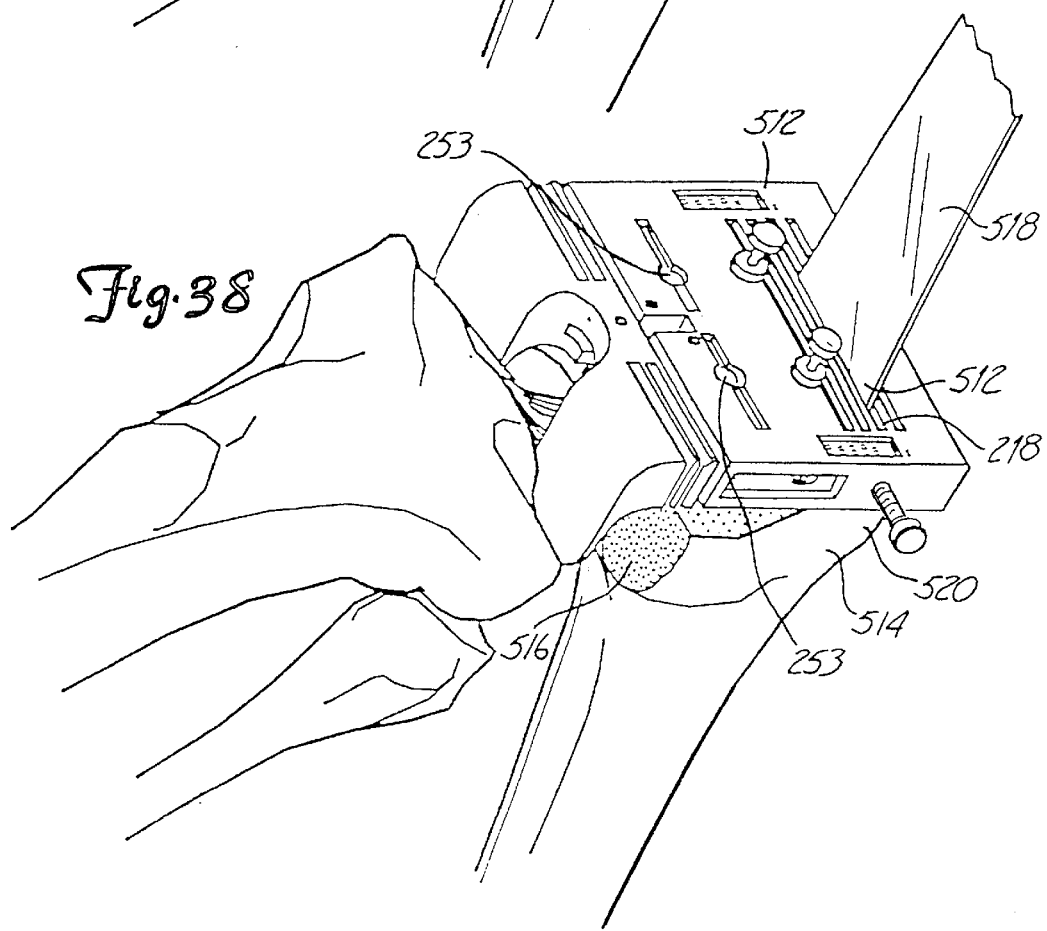

DEVICE AND METHOD FOR DISTAL FEMUR CUTTING AND PROSTHESIS MEASURING

This is a Continuation of application Ser. No. 08/606,270 filed Feb. 23, 1996, now abandoned.

FIELD OF THE INVENTION

The invention relates to improved instruments for preparing a knee for the placement of prostheses. More specifically, the invention relates to improved cutting guides and prosthesis measuring devices for assisting with the resection of the distal end of a femur in preparation for the placement of a prosthesis component at the distal end of the femur.

BACKGROUND OF THE INVENTION

The knee joint provides flexing of the leg where a lower bone called the tibia meets an upper bone called the femur. At the knee, the femur has two projections known as femoral condyles that engage with the articular cartilage at the upper end of the tibia. Degeneration of the cartilage contact surfaces on the tibia and the femur can cause pain, swelling and limited range of motion. During total knee arthroplasty, i.e., replacement surgery, the two surfaces joining at the knee are replaced with a prosthesis. The first step in this process is the removal of some of the diseased cartilage and underlying bone that is replaced by the prosthesis with its synthetic materials. The distal end of the femur is cut in order to provide clearance for a femoral component of the knee prosthesis that provides a new surface at the distal end of the femur.

A typical femoral prosthetic component fits over the distal end of the femur and curves over the anterior and posterior portions of the femur near the distal end. Preparation of the bone for the placement of most femoral components involves a cut or resection at the distal end, a cut along anterior and posterior sides of the femur near the distal end and two angled (chamfer) cuts joining the distal end with the anterior and posterior sides respectively. A variety of approaches exist for making these cuts that may involve making the cuts in different orders. The common features of these methods is that a selection of the proper sized prosthetic femoral component must be made and the cuts must be properly placed for the selected component size.

Often, a hole is drilled into the center of the femur from the distal end. An intermedullary rod is then placed within this hole to provide a relatively reproducible base from which implant components are oriented and located within the joint. In one approach, an adjustable block is attached to the intermedullary rod to guide the distal femoral bone cut. The cut distal surface can then provide a base for the size measurements and the remaining cuts.

After the distal cut is performed, a sizing jig is used to select the proper sized femoral component based on the size of the bone. The sizing jig serves as a guide for the drilling of holes later to be used for attaching a cutting guide. The sizing jig may have two paddles for contacting the femoral condyles on the posterior femur and an anterior probe for contacting the anterior femoral cortex, which appears externally as a shallow groove flanked on both sides by ridges of bone on the anterior side of the femur. Typically, there is a separate cutting guide for each available size of prosthesis. The proper cutting guide is then set in place by inserting pegs on the cutting guide into the holes mentioned above, and the cuts are made. Either a single cutting guide is used for the anterior cut, the posterior cut and the two chamfer cuts, or multiple cutting guides can be used. A large number of sterilized cutting guides are needed for each surgery because the size needed is not known with certainty before the surgery begins.

Generally, the anterior cut should be made so as not to violate the anterior cortex, otherwise a serious weakening of the femoral bone could take place creating significant risk of fracture. However, it can be difficult to perform the cuts without damaging the anterior cortex when the bone size is between available prosthesis sizes. The surgeon must use great care and judgment in aligning the cut, or, alternately, multiple cuts are required to progress to the desired final surface.

The cuts can be made with a small amount of rotation relative to the plane between the natural condyles. Such rotation reduces the chance of dislocation of the knee cap (patella). The rotation can be obtained either by using a cutting guide placed at the angle or by using a straight cutting guide and rotating the placement of the holes for the anchoring pegs. In principle, the rotation can be designed into the final prosthesis. In any case, performing the cuts to obtain the proper orientation can be very difficult if the cartilage on the posterior femoral condyles is unevenly worn because the posterior paddles of the sizing jig abut against the two unevenly worn posterior femoral condyles.

U.S. Pat. No. 4,892,093 (Zarnowski et al.) discloses a cutting guide for making the anterior femoral cut, the posterior femoral cut, the anterior chamfer cut and the posterior chamfer cut. The cutting guide has two posts which fit into corresponding holes drilled in the distal end of the femur, and the guide is further secured with a screw inserted into the distal end of the femur. The post holes must be positioned properly before the cutting guide is used. Using a single cutting guide for all four cuts provides a more accurate relationship between the different cuts while reducing the time required for the cuts. However, the cutting guide does not provide any flexibility in the placement of the cuts, so a different cutting guide must be used for cuts corresponding to each prosthesis size.

U.S. Pat. No. 4,759,350 (Dunn et al.) describes a system of instruments for preparing the distal femur and proximal tibia for receiving components of the knee prosthesis. The system uses the femoral intermedullary canal as a reference for the femur cuts. The system is designed to make a first cut of the femur along the anterior face of the distal end of the femur. The second cut is at the distal cut on the distal end of the femur. A gauge is used to select from six sizes for the eventual prosthesis component for the femur. A finishing cutting guide is selected based on the size read from the gauge, and the finishing cutting guide is used to perform a posterior cut, two chamfer cuts and a second anterior cut. The system described requires that two anterior cuts are ultimately performed to obtain the proper distal surfaces for the placement of the prosthesis. The cutting guide has a ledge for contacting the cut anterior surface to prevent motion of the cutting guide. The guide also has two pegs which fit into holes drilled into the distal end of the femur.

U.S. Pat. No. 4,938,762 (Wehrli) and U.S. Pat. No. 4,567,885 (Androphy) involve resection systems where a cutting block is transferred to guide cuts on both the tibia and the femur. These systems have the disadvantage that the cutting block either has to be selected based on the size of the prosthesis component or they must be explicitly adjusted for each cut to accommodate the different size prostheses. These systems are difficult to use and leave considerable room for error.

U.S. Pat. No. 5,002,547 (Poggie et al.) describes a modular apparatus for preparing both the tibia and femur for a knee prosthesis. The distal end of the femur is the first surface of the femur that is cut. A sizer is placed against the cut surface at the distal end to determine the correct size for the prosthesis. Then, a guide is placed against the cut distal end of the femur, and is used for drilling holes based on the selected size for the prosthesis component. The guide has a set of holes for each size component. An appropriately sized cutting guide is selected. The cutting guide is used to perform the anterior cut, the posterior cut and the two chamfer cuts.

U.S. Pat. No. 4,457,307 (Stillwell) describes a complicated device for performing all needed cuts on the tibia and the femur. The device includes a power saw and all the adjustments needed to align the saw. While this instrument is very versatile, it is very awkward and difficult to use. Bolts must be loosened to position the instruments, and then tightened in order to make the cuts. Furthermore, while the instrument can be adjusted to accommodate different size prosthesis components, calculations must be performed in order to make the adjustments.

U.S. Pat. No. 4,703,751 (Pohl) presents a cutting guide for cutting the distal end of the femur as a first step of preparing the bone for a prosthesis component. The resection guide provides for severe condylar deficiency. The cutting guide has a cutting plate that pivots relative to a support plate. The cutting plate locks relative to the support plate at a predetermined angle. The support plate attaches to an intramedullary rod for alignment of the cut. A reference bar pivots relative to the rod and contacts both the lateral and medial condyles. A plurality of reference bars are selected to provide the appropriate thickness of the cut to avoid cutting excessive material from the condyles. Bolts within the reference bar enable the surgeon to fine tune the cutting distance and similarly to make it easier to compensate for the particular deterioration of one of the condyles. There is no suggestion of how to adapt the apparatus to make other cuts on the femur.

U.S. Pat. No. 4,722,330 (Russell et al.) discloses an apparatus which attaches to an intramedullary alignment rod for providing an anterior cut, a posterior cut and two chamfer cuts. The apparatus has a main body which is attached and aligned once. The other parts are attached to the main body as needed. The apparatus has an adjustment relative to the anterior cortex to provide for proper location of the cuts on the anterior and posterior surfaces. The main body has a fixed relationship between the cutting guides for the different cuts. Therefore, a different main body would be needed to make cuts for different size femoral prosthesis components.

U.S. Pat. No. 5,364,401 (Ferrante et al.) describes a system for resecting the femur where various cutting guides can be sequentially placed on a support that is initially positioned on the bone. The final step in the preparation uses a cutting block that can make an anterior cut, a posterior cut and two chamfer cuts. The cutting block can be moved along the cut distal end of the femur relative to an alignment portion attached to the anterior part of the femur. This structure, which allows motion, aides in aligning the cuts to avoid cutting too much bone from the anterior surface. The cutting block must be selected to correspond to a selected size prosthesis component.

The above described instruments for preparing the distal end of the femur are all deficient in that they are either difficult to use, not versatile in their placement or both.

SUMMARY OF THE INVENTION

The resection instruments of this invention provide considerable versatility and ease of use while yielding accurate cut surfaces for the placement of femoral prosthesis components. The instruments generally have paddles or the like for contacting the posterior side of the femoral condyles or the corresponding intercondylar notch, and are designed for placement on the bone bed at the distal cut on the distal end of the femur. The posterior femoral condyles and anterior femoral cortex provide the reference points for measurements and cuts of the femur. The instruments are used for measuring the desired size of the femoral prosthesis component and/or making the appropriate cuts at the distal end of the femur for the selected size of the femoral prosthesis component. The cuts can include posterior, anterior, posterior chamfer and anterior chamfer cuts.

One embodiment of the femoral resection instrument provides precise anterior and posterior cuts of the femur appropriate for one of several size prosthesis components without the need for separate cutting guides. Versions of this embodiment have several cutting guides spaced appropriately for the cuts corresponding to the different size prosthesis components. Another version of this embodiment has a body portion that can move relative to the condyle paddles to select the proper placement for the cut, given the desired prosthesis component size.

Another embodiment provides for shifting the cutting locations of both the posterior and anterior cuts by a portion of the distance between sizes of the prosthesis components while maintaining the reference position relative to the posterior part of the condyles and corresponding intercondylar notch. One version of this embodiment can use two cutting guides for the posterior cut and a movable portion that shifts the anterior cutting guides by the same amount as the distance between the two posterior cutting guides, which is a portion of the distance between component sizes. An alternative would be to shift the posterior cutting guides rather than provide multiple cutting guides. Similarly, multiple sets of anterior cutting guides can be provided rather than moving the anterior cutting guides to a shifted position. Shifting the cuts prevents the removal of excess bone from the anterior side of the femur at the femoral cortex while maintaining the convenience of using the condyles to reference the instrument.

Another embodiment has an adjustable paddle so that the femoral resection instrument can be adjusted to the correct orientation when the femoral condyles are worn unequally. It is preferred to use an intercondylar paddle as the adjustable paddle along with one or two stationary posterior femoral condylar paddles. Alternatively, one of the posterior femoral condylar paddles can be adjustable. These features may also be combined, if desired.

The invention includes a method of positioning the femoral resection instrument using paddles that contact at least one of the posterior femoral condyles. The instrument has posterior and anterior cutting guides, and enables placement of the anterior cutting guide so that the anterior cut will be properly located for a selected size of a femoral prosthesis component.

Another method of the invention involves the similar placement of a femoral resection instrument relative to the femoral condyles. However, this second method is appropriate when the measured size of the distal end of the femur is between available sizes of the femoral prosthesis components. In this method the posterior and anterior cuts at the distal end of the femur are separated by a distance corresponding to a portion of a prosthesis component size so that the anterior cut will not remove material from the anterior side of the distal end of the femur in excess of what is proper.

BRIEF DESCRIPTION OF THE DRAWINGS

FIG. 5 is a side view of the posterior body portion of the femoral resection instrument with structure of the key hole shown in phantom lines;

FIG. 6 is a top-front perspective view of the posterior body portion of the femoral resection instrument;

FIG. 7 is a rear plan view of the adjustable intermedullary paddle with a hole from the top shown in phantom lines;

FIG. 8 is a side plan view of the adjustable intermedullary paddle with the holes from the top shown in phantom lines;

FIG. 9 is a front-top perspective view of the adjustable intermedullary paddle;

FIG. 10 is a rear-bottom perspective view of the adjustable intermedullary paddle;

FIG. 11 is a perspective view of a handle;

FIG. 12 is a bottom plan view of the anterior body portion of the femoral resection instrument with structure on the top surface and internal structure of the anterior keyhole shown in phantom lines;

FIG. 13 is a front view of the anterior body portion of the femoral resection instrument;

FIG. 14 is a cut away sectional view along lines 14—14 of FIG. 12;

FIG. 15 is a side view of the anterior body portion of the femoral resection instrument;

FIG. 16 is a sectional view along lines 16—16 of FIG. 12 where the outline of the full side view of anterior portion of the femoral resection instrument is shown in phantom lines;

FIG. 17 is a sectional view along lines 17—17 of FIG. 12;

FIG. 37 is a perspective view of the femoral resection instrument on the distal end of a femur being used to cut the posterior surface of the distal end of the femur using an alternative cutting slot for the case where the bone is in between the available implant component sizes;

FIG. 38 is a perspective view of the femoral resection instrument on the distal end of a femur being used to cut the anterior surface of the distal end of the femur using a cutting guide for a particular size prosthesis component.

DETAILED DESCRIPTION OF THE INVENTION

The femoral resection instruments of the invention overcome many of the deficiencies of previous resection sizers and cutting guides. The femoral resection instruments serve as a sizing tool or a cutting guide, or both, for performing cuts at the distal end of the femur possibly including an anterior cut, a posterior cut, an anterior chamfer cut and a posterior chamfer cut. The femoral resection instruments are generally designed for use following an initial distal femur cut which provides a flat surface at the distal end of the femur.

An important attribute of the femoral resection instruments of this invention is the ability to guide cuts for different size femoral prosthesis components using a single tool in a fixed position on the distal end of the femur. A further attribute includes positioning the instruments with respect to the posterior femoral condyles while permitting adjustment for femur sizes between femoral prosthesis component sizes, thus avoiding removal of excess bone from the anterior femoral cortex. Also, the preferred femoral resection instruments can be adjusted to account for uneven wear of the posterior femoral condyles, using a combination of fixed and adjustable paddles. A preferred embodiment may comprise a single instrument having all of the above features. However, other preferred embodiments of the femoral resection instruments may have any combination of these novel individual features, or even one of the features alone.

Figure 1:
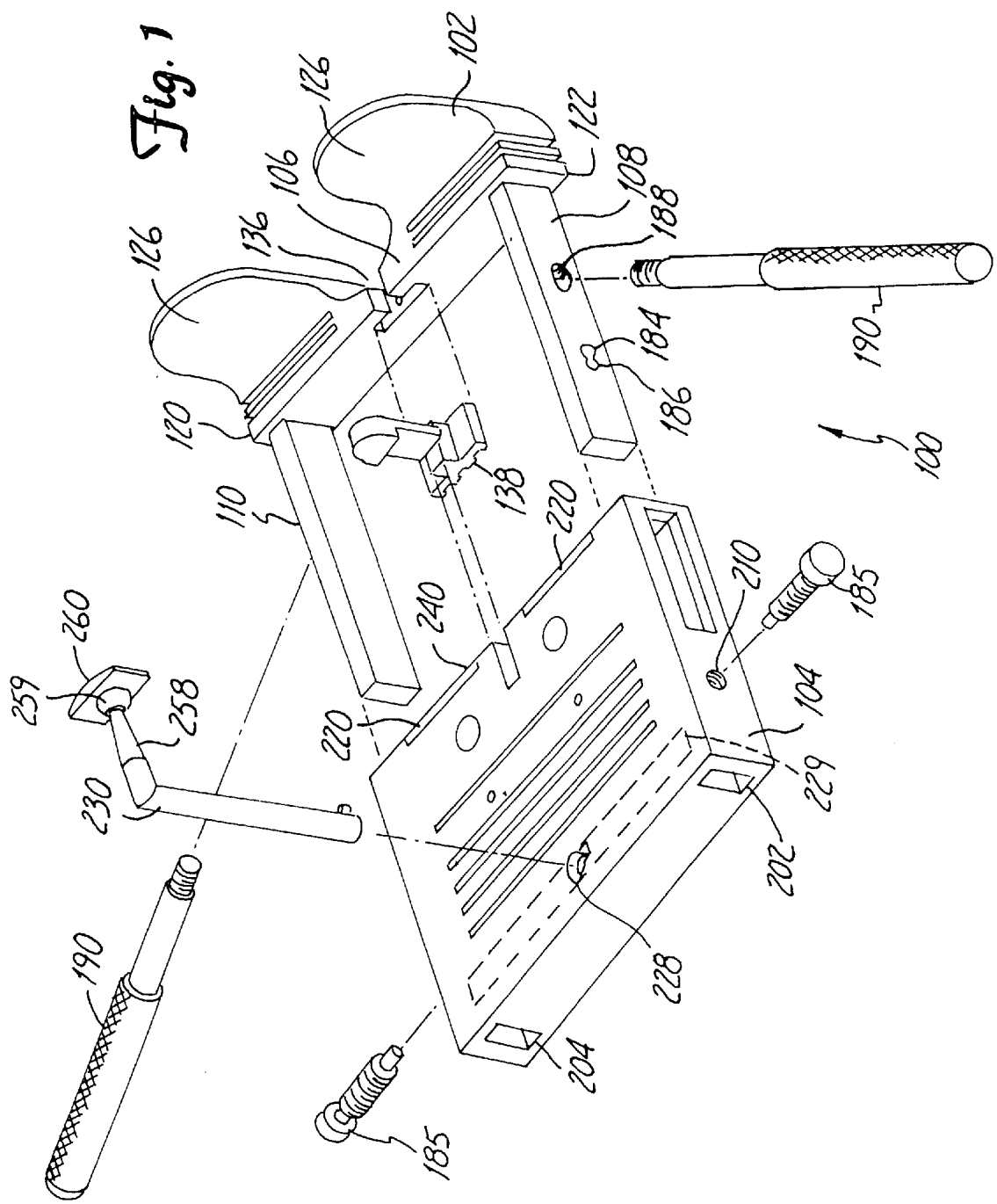
FIG. 1 is an exploded bottom-rear perspective view of one embodiment of the femoral resection instrument.
Figure 2:
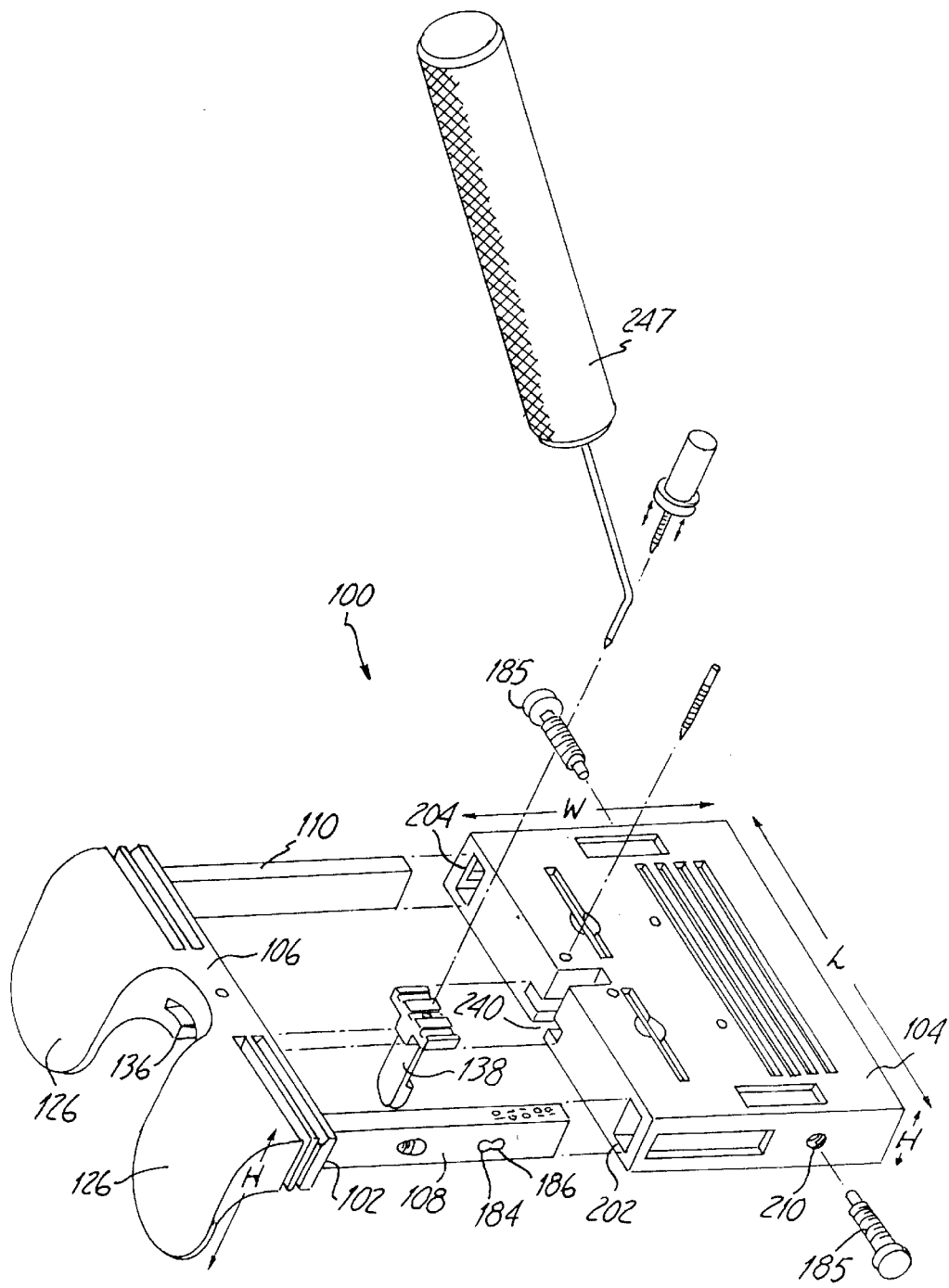
FIG. 2 is an exploded top-front view of an embodiment of the femoral resection instrument.
Figure 3:
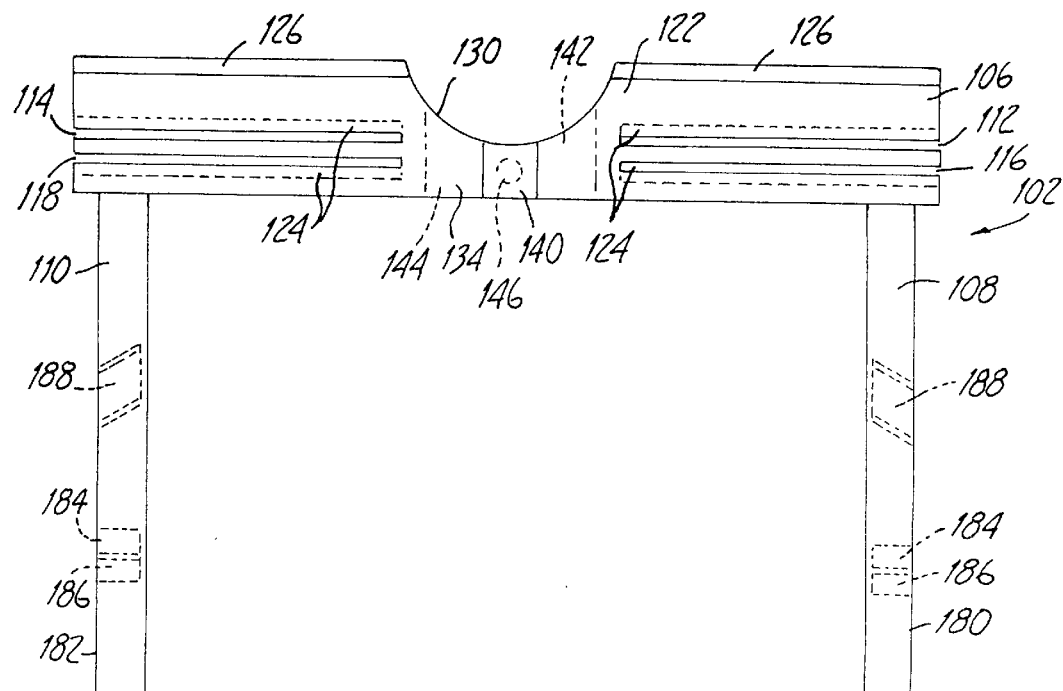
FIG. 3 is a bottom plan view of a posterior body portion of a femoral resection instrument where holes within the elongated prongs, widened openings on the top surface of the cutting guides and internal structure of the posterior key are shown in phantom lines.

One embodiment of femoral resection instrument or guide 100 is shown in FIGS. 1 and 2. Instrument 100 has a plurality of body portions comprising, in this embodiment, at least a posterior body portion 102 and an anterior body portion 104. Posterior body portion 102 has a posterior cutting block 106, a right elongated attachment prong 108, and a left elongated attachment prong 110. FIG. 3 discloses posterior cutting block 106 having a plurality of cutting guides, comprising a first right cutting guide 112, a first left cutting guide 114, a second right cutting guide 116 and a second left cutting guide 118. Cutting guides 112, 114, 116, 118 extend through block 106 from top surface 120 to bottom surface 122. In this embodiment the cutting guides are generally perpendicular to surfaces 120, 122. At top surface 120, the cutting guides 112, 114, 116, 118 have a sloped widened opening 124 to facilitate the insertion of a cutting blade into the cutting guides. This is shown, for example, in FIG. 6.

The size of the instrument or guide 100 may vary. In one embodiment, instrument 100 comprised a length L of between about 80 millimeters (mm) and about 120 mm, a width W of about 40 mm to about 80 mm for the anterior body portion 104 and about 10 mm to about 30 mm for the posterior body portion 102, and a height H of about 12 mm to about 20 mm for anterior body portion 102 and about 25 mm to about 45 mm for the largest dimensions of posterior body portion 104. In one embodiment, some of the dimensions were about L=101 mm, W=61 mm (anterior body portion) and 17 mm (posterior body portion).

Figure 4:
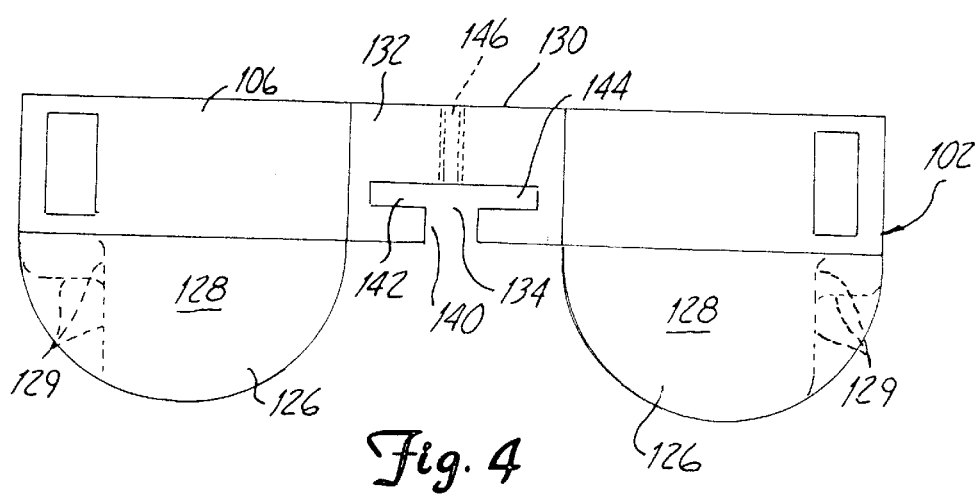
FIG. 4 is a rear view down the elongated prongs of the posterior body portion of the femoral resection instrument with a threaded hole in the posterior hole key shown in phantom lines.

Two stationary condyle paddles 126 extend from bottom surface 122 of posterior cutting block 106, as further shown in FIG. 6. Stationary condyle paddles 126 have an interior face 128, shown in FIG. 5, for contacting one of the posterior femoral condyles. The stationary condyle paddles 126 are preferably relatively thin and rounded at their bottom as displayed in FIGS. 5 and 6, although the exact shape is not as significant as the requirement that the paddles provide an interior face 128 properly shaped for contacting the posterior femoral condyles. Although, in certain patients it may be quite important to use paddles shaped with reduced area along, for example, cut-lines 129 in FIG. 4, to avoid undesired contact with various soft tissue around the joint. It may also be desirable to smooth or round any sharp edges at corners or other protrusions on the instrument.

Posterior cutting block 106 preferably has an indentation 130 between the stationary condyle paddles 126 as shown in FIGS. 1–6. Surface 132 of indentation 130 has an opening into a keying aperture 134. Keying aperture 134 is sized for acceptance of a key 136 connected to an adjustable intermedullary paddle 138, shown in FIGS. 7–10. Keying aperture 134 has walls forming a channel 140 and wings 142, 144. Locking pin aperture 146, shown in FIGS. 4 and 5, opens into aperture 134 from top surface 120 of posterior cutting block 106. Aperture 146 accepts a pin, screw or similar means, which, when advanced, contacts a portion (such as central groove 150) of adjustable intermedullary paddle 138, and thereby fixes the position of paddle 138 within aperture 134.

Figure 20:
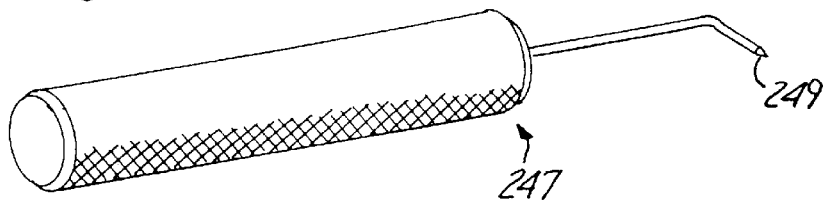
FIG. 20 is a perspective view of an advancing lever.

Adjustable intermedullary paddle 138 has a paddle 148, key 136 and connecting portion 151 joining paddle 148 and key 136. Key 136 is designed to fit into keying aperture 134 in the posterior cutting block 106. Key 136 has two holes 152 opening at its top surface 153, with top surface 153 having various optional sizes as shown by the different size outlines of FIG. 8. Holes 152 receive tip 249 of advancing lever 247, shown in FIGS. 2 and 20. Advancing lever 247 moves the adjustable intermedullary paddle 138 within mating keyholes in the posterior body portion 102 and anterior body portion 104.

Referring again to FIGS. 3–6, right and left elongated attachment prongs 108, 110 extend away from the posterior cutting block 106 portion comprising cutting guides 112, 114, 116, 118. Attachment prongs 108, 110 are depicted with rectangular cross sections, but other shapes may be used if the anterior body portion 104 is appropriately modified. Attachment prongs 108, 110 have outer surfaces 180, 182 respectively, which define two prong holes 184, 186. The distance between the centers of prong holes 184 and 186 preferably corresponds to the distance between the respective centers of cutting guides 112 and 116 and between the respective centers of cutting guides 114 and 118. This distance corresponds to roughly half of the distance between femoral component sizes. The diameters of holes 184 and 186 should be approximately the same and preferably should be selected to minimize the overlap of holes 184,186. Angled, threaded holes 188 also open onto the outer faces 180, 182, and will be further described below.

Right and left elongated prongs 108, 110 provide mechanical cooperation between posterior body portion 102 and anterior body portion 104. Prong holes 184, 186 are used to lock the posterior body portion 102 with respect to anterior body portion 104 in one of two positions by appropriately selecting one of the prong holes 184, 186 for engagement with springing screws 185, shown in FIGS. 1, 2 and 19. Springing screw 185 has a head 187, a threaded portion 189 and a tip 191. Pulling on the head 187 moves the tip 191 into the threaded portion 189. Other similar retaining means could be suitable for use with prong holes 184, 186.

Holes 188, which in one embodiment are angled and threaded, are used for the attachment of handles 190, shown in FIGS. 1 and 11, to the femoral resection guide 100. Handles 190 have means for engaging holes 188, which in this embodiment comprises a threaded end 192 for engaging threaded holes 188. The top surface of the elongated attachment prongs 108, 110 have size markings 194, shown in FIG. 6, that are useful in determining the correct size of the femoral prosthesis component to be used for the particular sized femur undergoing the surgery. The location or positioning of the retaining means comprising springing screws 185 or handles 190 may be altered to optimize the ergonomics, although alterations or repositioning may also require repositioning of the windows discussed below.

Figure 18:
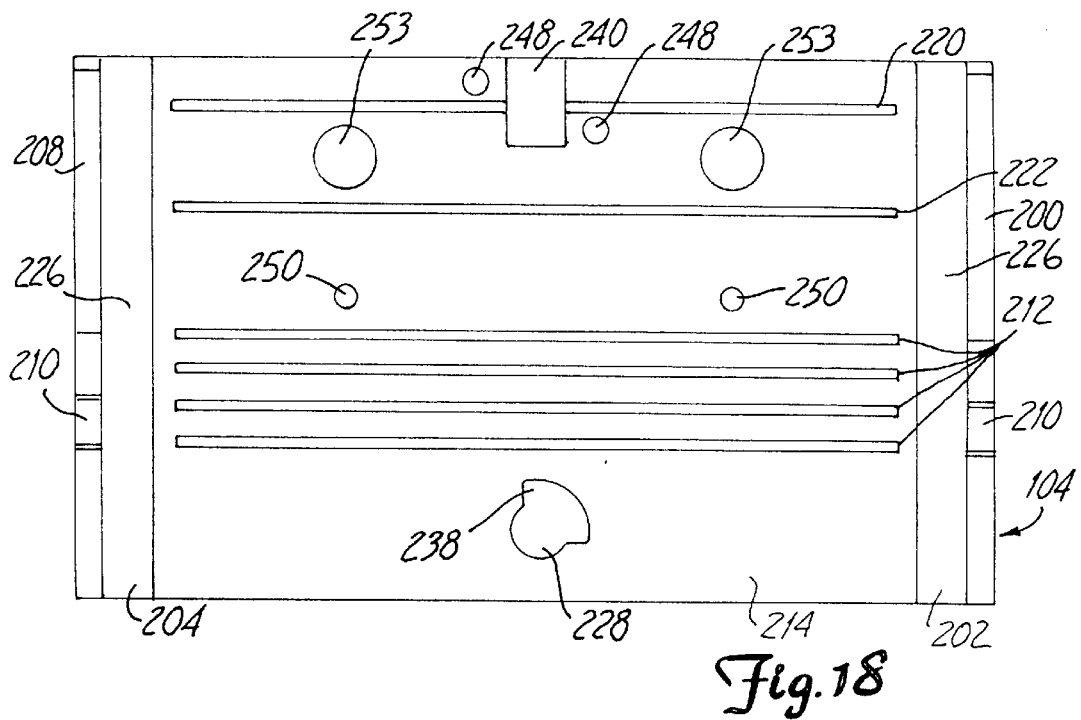
FIG. 18 is a sectional view along lines 18—18 of FIG. 13.

Referring to FIGS. 3 and 18, the anterior body portion 104 has right channel 202 and left channel 204 for the insertion of elongated attachment prongs 108, 110. Right window 206 and left window 208 expose a portion of the respective channels 202, 204 so that angled, threaded holes 188 are accessible by handles 190 when the elongated attachment prongs 108, 110 are within channels 202 and 204. Threaded positioning holes 210 provide access for retaining means, such as the tip 191 of a spring screw 185, to holes 184, 186 when the elongated attachment prongs 108, 110 are within channels 202, 204.

Figure 19:
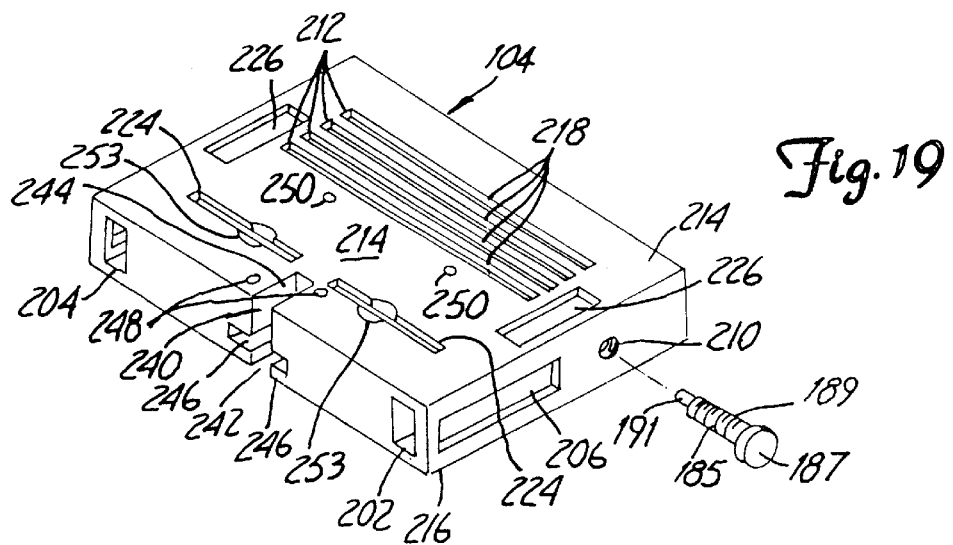
FIG. 19 is a top-front perspective view of the anterior portion of the femoral resection apparatus.

Anterior body portion 104 has a plurality of anterior cutting guides 212 extending straight through the anterior body portion from the top surface 214 to the bottom surface 216, as shown in FIGS. 17–19. At the top surface 214, the anterior cutting guides 212 have widened openings 218 to facilitate the insertion of a cutting blade into the cutting guides. The widened openings may be configured in various shapes, as desired. Each of the four anterior cutting guides 212 is appropriate for a certain size of the femoral prosthesis component. Once the appropriate size of the femoral prosthesis component is selected, the corresponding anterior cutting guide 212 is used to perform an anterior cut to the distal end of the femur. While four anterior cutting guides 212 are depicted in the Figures, other numbers of cutting guides greater than two can be used. Optimum advantage occurs when two or more cutting guides exist. The number of anterior cutting guides 212 can be selected to correspond to the number of sizes of femoral prosthesis components or some subset of the number of sizes of the femoral prosthesis components.

Anterior body portion 104 also has a posterior chamfer cutting guide 220 and an anterior chamfer cutting guide 222. Posterior chamfer cutting guide 220 may extend either partially across the width of anterior body portion 104 as shown in FIG. 1, or more fully across the width, as shown in FIG. 12. The chamfer cutting guides 220, 222 angle through the anterior body portion 104, as shown in FIGS. 13 and 14. The chamfer cutting guides 220, 222 meet at the top surface 214 to form a widened opening 224, to facilitate insertion of the cutting blade. At the bottom surface 216, the chamfer cutting guides 220, 222 are separated in order to direct the cut in the appropriate direction. The top surface 214 of the anterior body portion 104 has windows 226 exposing a portion of the channels 202, 204 such that size markings 192 on elongated prongs 108, 110 can be visible from the top surface 214, as depicted in FIGS. 9 and 16.

FIGS. 1, 12 and 18, disclose alternate embodiments 228, 229 of anterior keyholders. Each provides for the attachment of anterior femoral target 230, shown in FIGS. 21–23. Key holder 228 comprises a surface which intersects the bottom surface 216 of the anterior body portion 104. The opening of key holder 228 has an elongated portion 232 extending from a circular portion 234. The circular portion 234 of the opening leads to a circular cavity extending part way through the anterior body portion 104. The elongated portion 232 allows for the insertion of a notch 236 on the end of anterior femoral target 230. Within the anterior body portion 104, the key holder 228 has an arc section 238 with an edge configured below the elongated portion 232 of the opening. Arc section 238 presents a space for the rotation of notch 236 within the anterior key holder 228 to secure the attachment of anterior femoral target 230 with the anterior body portion 104. The embodiment of anterior key holder 229 provides for a slidable feature along the width of anterior body portion 104.

Posterior key hole 240 near the front of anterior body portion 104, in some sense, provides an extension of key hole 134, although the posterior body portion 102 and the anterior body portion 104 are separated in certain configurations. Posterior key hole 240 has a lower channel 242, an upper channel 244 and wings 246, as shown in FIGS. 13, 14 and 19. Two threaded holes 248 connect the top surface 214 of anterior body portion 104 with the wings 246 of posterior key holes 240. Threaded holes 248 are in a staggered relationship. Alternate embodiment retaining means, shown in FIG. 2 as either a thumbscrew mechanism, which is also useful as an advancing member, or one or more pin structures extended through threaded holes 248, can be used to lock the intermedullary paddle 138 in its position. Holes 248 could also not be threaded, and accept a pin for fixation. An advancing lever 247, depicted in FIG. 20, has a tip 249 for engaging holes 152 to move the adjustable intermedullary paddle 138 within posterior key hole 240 by way of upper channel 244. The advancing lever 247 can be replaced by a variety of similar devices for engaging the holes 152 to move the adjustable intermedullary paddle 138. Alternatively, it is possible to use a thumbscrew.

The intermedullary paddle 138 can have different configurations as long as the configurations of key hole 134 and posterior key hole 240 are changed correspondingly. It is possible to design the femoral resection instrument 100 with only either a key hole 134 (perhaps extended forward) or posterior key hole 240, with modifications to the intermedullary paddle 138 to allow it to contact the intermedullary notch in the femur. For example, it may be necessary then to change the relationship of paddle 148 to key 136 by elongating or angling connecting portion 150. Furthermore, it is possible to design the intermedullary paddle 138 to have a screw adjustment to alter the extension of the paddle 138, with the base of the paddle 138 fixed on the posterior body portion 102. Also, it is possible to design the posterior femoral condyle paddles to be adjustable rather than stationary to replace or augment the adjustable intermedullary paddle 138. The adjustable feature of the posterior femoral condyle paddles can be similar to the various possible constructions of the adjustable feature of the intermedullary paddle 138.

Fastener holes 250 pass through the anterior body portion 104. Pins 252 or comparable fasteners can be optionally passed through fastener holes 250 and into the distal femoral bone to stabilize the femoral resection guide 100 on the distal end of the femur. The size of the pins is not particularly important, but it would be preferred to use the shortest pins 252 that provide adequate stability. These fastener holes 250 could also be angled as they pass through the anterior body portion 104, and could be located anywhere on the anterior body portion 104, as long as they don't disturb the functions of the resection guide. Drill holes 253 provide a guide for the drilling of holes into the distal femoral bone for posts on the underside of the eventual femoral prosthesis component. Drill holes 253 pass from the top surface 214 through to the bottom surface 216. The location of drill holes 253 is determined by the design of the femoral prosthesis component. Some designs of femoral prosthesis components may require only a single drill hole, more than two drill holes or no drill holes.

Figures 21, 22, 23:
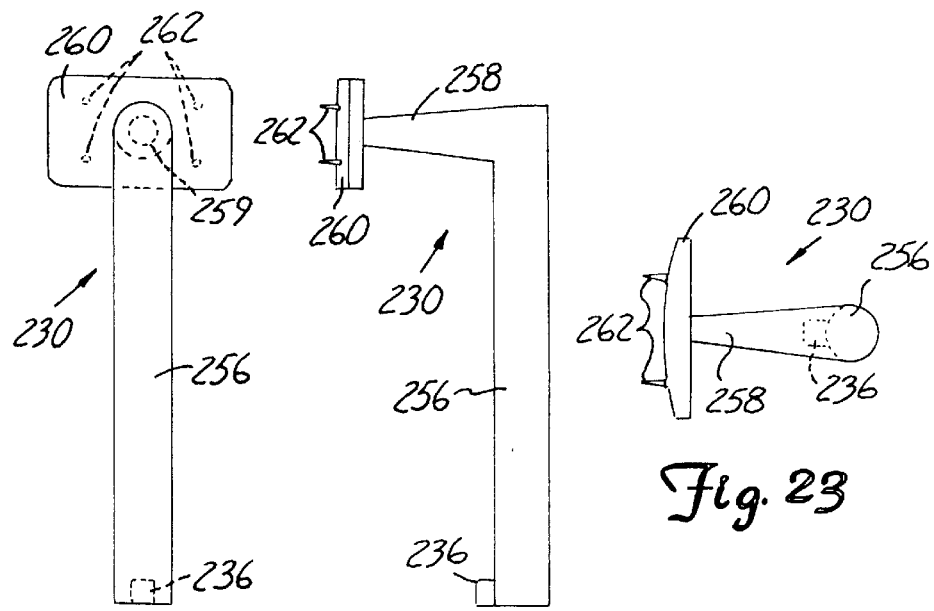
FIG. 21 is a rear plan view of an anterior femoral target with hidden structure shown in phantom lines.
FIG. 22 is a side elevation view of the anterior femoral target.
FIG. 23 is a top plan view of the anterior femoral target with hidden structure shown in phantom lines.

Referring again to FIGS. 21–23, the anterior femoral target 230 has an elongated shaft 256 with the notch 236 at one end for attachment to the anterior body portion 104. An arm 258 extends from the other end of the shaft 254. The arm 258 has a plate 260 at its end. Plate 260 is shaped to fit into the shallow groove on the anterior surface of the femur. Plate 260 has, in one embodiment, a plurality of points 262 projecting from its surface away from arm 258. The points 262 contact the anterior surface of the femur when the femoral resection guide 100 is being used to determine the appropriate size of the femoral prosthesis component. Another embodiment of plate 260 has a concave surface, and may have no points projecting therefrom. The points 262 help to prevent slipping of the anterior femoral target as it is used in the sizing of the bone. The dimensions of the anterior femoral target 230 are selected to align the anterior body portion 104 during the sizing operation. One embodiment of anterior femoral target 230 has a plate 260 that can tilt with respect to arm 258 to provide better contact with the anterior surface of the femur. FIG. 21 depicts a ball and socket connection 259 between the arm 258 and the plate 260 to provide the tilting degree of motion. Structures other than a ball and socket may be used to supply the tilting degree of freedom. Also, plate 260 can be fixed to arm 258, with the tilting supplied by the motion of the tab 236 within the anterior keyhole 228.

The relationships between portions of the femoral resection instrument 100 can be seen in the exploded views of FIGS. 1 and 2. The operation of the femoral resection apparatus 100 is now further described below, along with some alternate embodiments of the device components.

Figure 24:
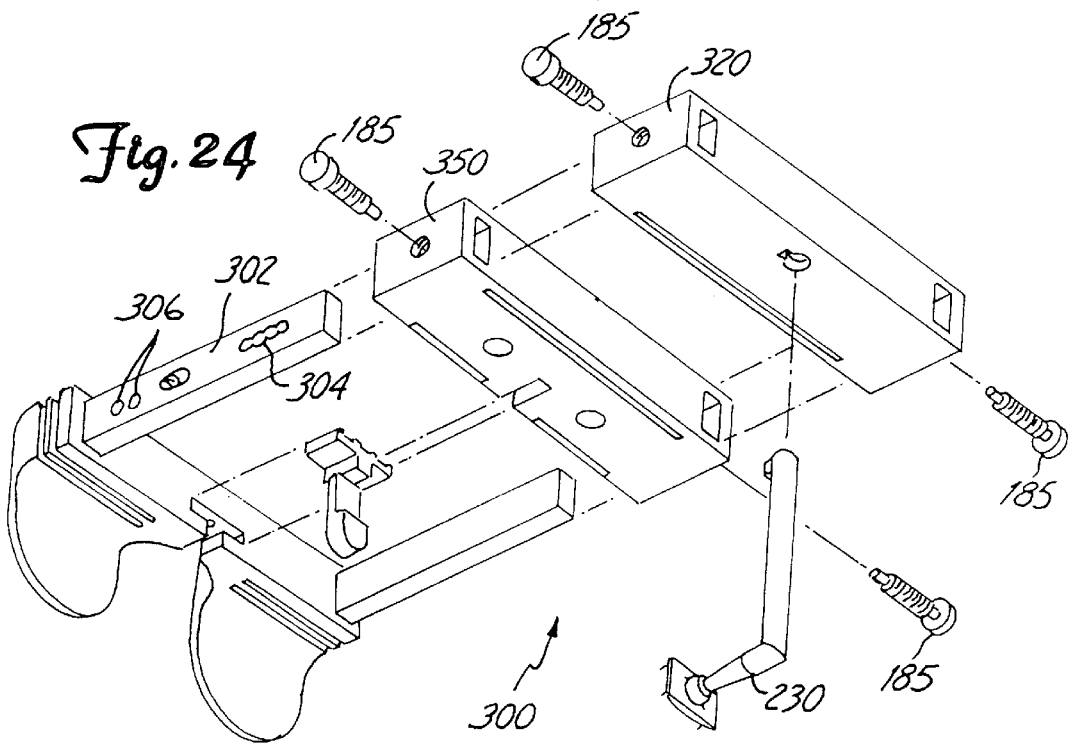
FIG. 24 is a rear-bottom exploded perspective view of the alternative embodiment of the femoral resection instrument with both anterior body portions shown with their relationship with respect to the posterior body portion.
Figure 25:
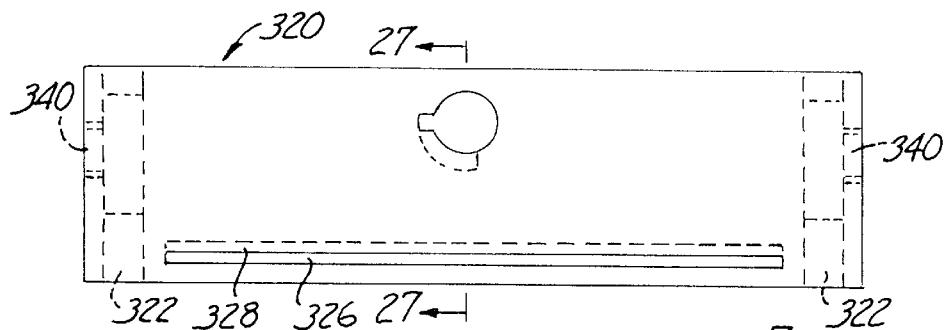
FIG. 25 is a bottom plan view of a first anterior body portion of an alternative embodiment of the femoral resection instrument with structure at the top surface and the channels near the edges shown in phantom lines.
Figure 26:
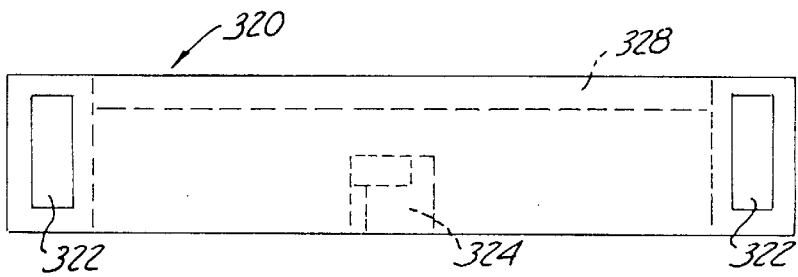
FIG. 26 is a rear view of the first anterior portion of the alternative embodiment of the femoral resection instrument with hidden structure shown in phantom lines.
Figure 27:
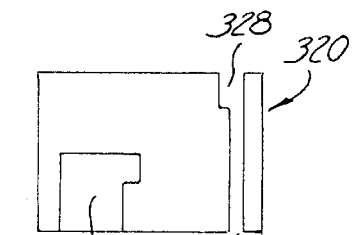
FIG. 27 is a sectional view taken along lines 27—27 of FIG. 25.
Figure 28:
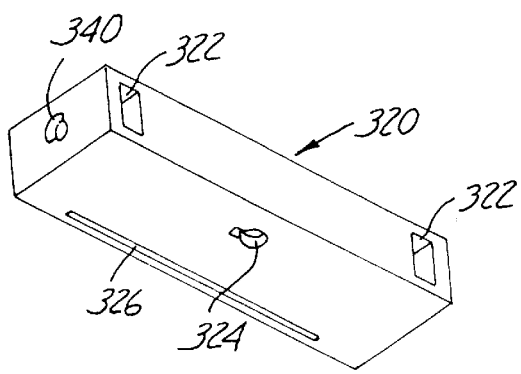
FIG. 28 bottom rear perspective view of the first anterior body portion of the alternative embodiment of the femoral resection instrument.
Figure 29:
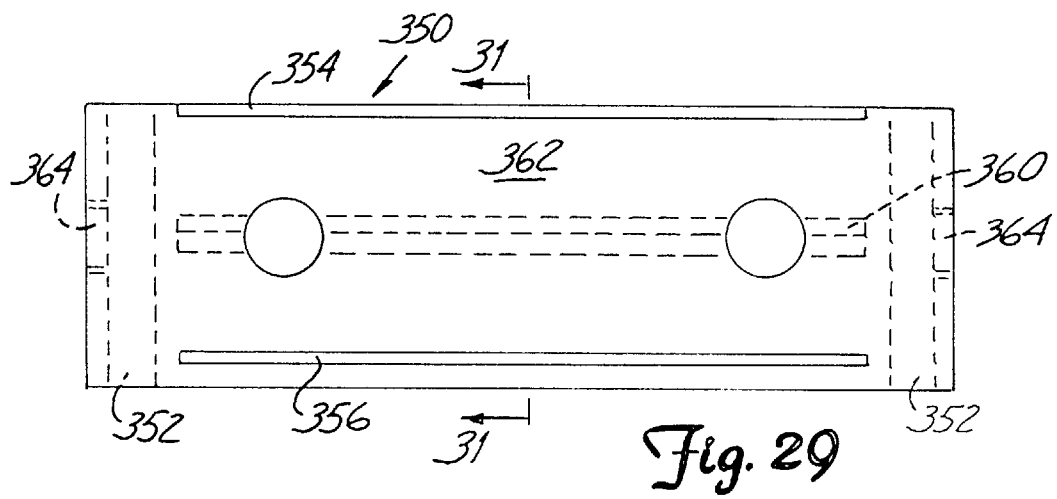
FIG. 29 is bottom plan view of a second anterior portion of the alternative embodiment of the femoral resection instrument with structure at the top surface and other hidden structure shown in phantom lines.
Figure 30:
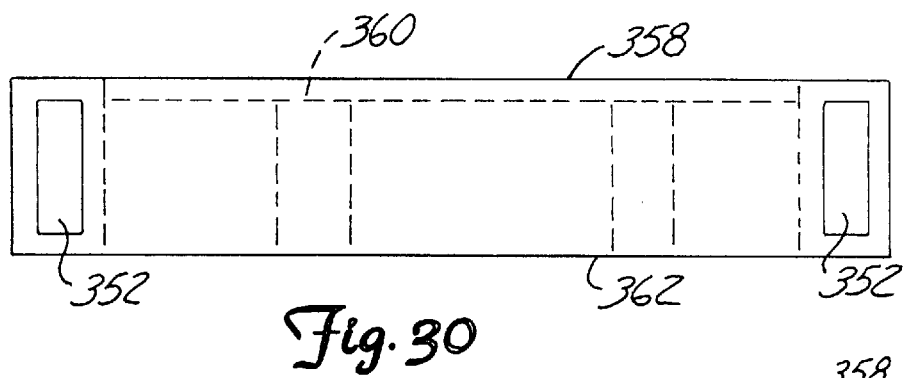
FIG. 30 is a rear view of the second anterior portion of the alternative embodiment of the femoral resection instrument with hidden structure shown in phantom lines.

In FIG. 24, femoral resection instrument 300 has the anterior cutting guide and the chamfer cutting guide placed on different body portions that are used sequentially. The anterior body portions engage a posterior body portion 302 similar to posterior body portion 102. Posterior body portion 302 has a plurality of holes 304, and in this embodiment there are four holes 304, for engaging the tip 191 of spring screw 185 when the first anterior body portion 320 is engaged with the posterior body portion 302. The position of each hole 304 corresponds to a size of the femoral prosthesis component in the same sense as the four anterior cutting guides within anterior body portion 104. Additional holes 304 can be included for the intermediate measured sizes for the femoral prosthesis component if an alternative posterior cutting guide if used.

Holes 306 are used to engage spring screw 185 when the second anterior body portion 350 is engaged with the posterior body portion 302. These holes accommodate the use of the chamfer cutting guides on the second anterior body portion for intermediate femoral prosthesis component sizes. It is possible that more than two holes 306 may be desirable.

First anterior body portion 320 is further depicted in FIGS. 25–28. First anterior body portion 320 has channels 322 for engaging elongated prongs of the posterior body portion 302. Anterior key holder 324 has the same structure as key holder 228 and can secure an anterior femoral target 230 to anterior body portion 320. Sizing is performed in a similar fashion as within embodiment 100. First anterior body portion 320 has, in this embodiment, a single anterior cutting guide 326. Anterior cutting guide 326 has a widened opening 328 to facilitate the insertion of a cutting blade. Threaded holes 340 provide access for spring screw 185 to the holes 304.

Figure 31:
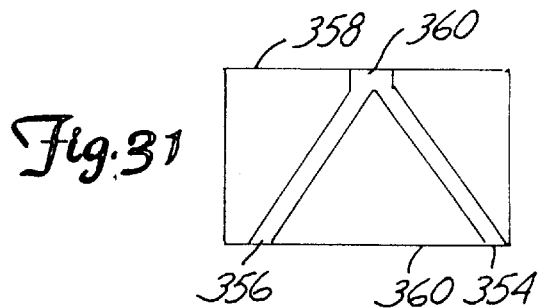
FIG. 31 is sectional view taken along lines 31—31 of FIG. 29.
Figure 32:
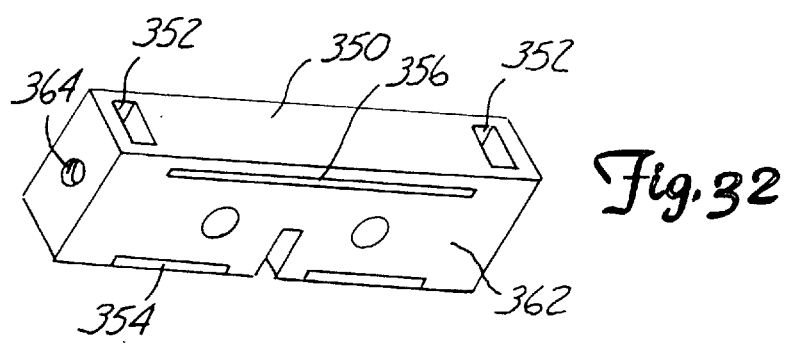
FIG. 32 is a rear-bottom perspective view of the second anterior body portion of the alternative embodiment of the femoral resection instrument.

A second anterior body portion 350 is depicted in FIGS. 29–32. Second anterior body portion 350 also has channels 352 for engaging elongated prongs of the posterior body portion 302. Second anterior body portion 350 has a posterior chamfer cutting guide 354 and anterior chamfer cutting guide 356. The chamfer cutting guides 354, 356 angle through second anterior body portion 350, as shown in FIG. 31. The chamfer cutting guides 354, 356 meet at the top surface 358 to form a widened opening 360, to facilitate insertion of the cutting blade. At the bottom surface 362, the chamfer cutting guides 354, 356 are separated in order to direct the cut in the appropriate direction. Threaded holes 364 provide access for spring screw 185 to the holes 306. The overall relationship between the various parts of the embodiments of the femoral resection instrument can be seen in the exploded view of FIG. 24.

Figure 33:
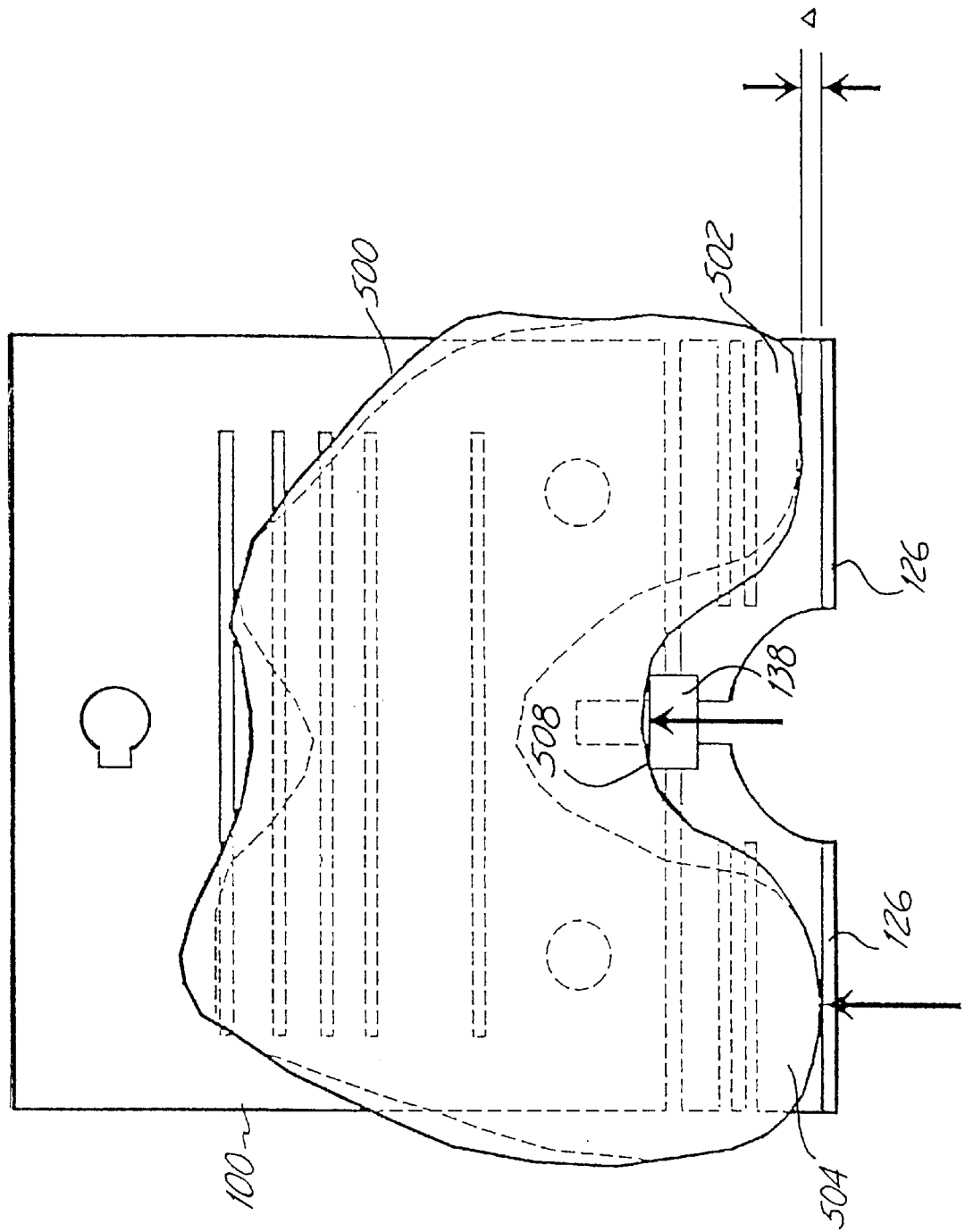
FIG. 33 is an axial view oriented down the femur, depicting the use of the adjustable intermedullary paddle to correct the orientation of the femoral resection instrument accounting for uneven wear of the femoral condyles, with hidden structure of the femoral resection apparatus and the variation of the femur shown in phantom lines.

FIG. 33 shows femoral resection guide 100 in use with a femur 500. The first step in the use of femoral resection guide 100 involves the adjustment of the alignment of the femoral resection guide 100, if required, due to uneven wear of the posterior femoral condyles 502, 504. For example, if one posterior femoral condyle 502 is worn more than the other posterior femoral condyle 504, the adjustable intermedullary paddle 138 is used to adjust for the uneven wear. Referring to FIG. 33, the less worn femoral condyle 504 will contact the appropriate stationary condyle paddle 126 and the adjustable intermedullary paddle 138 will contact the intercondylar notch 508. The other stationary condyle paddle 126 will be spaced apart from the more worn femoral condyle 502 by a distance Δ indicated in FIG. 33.

Figure 34:
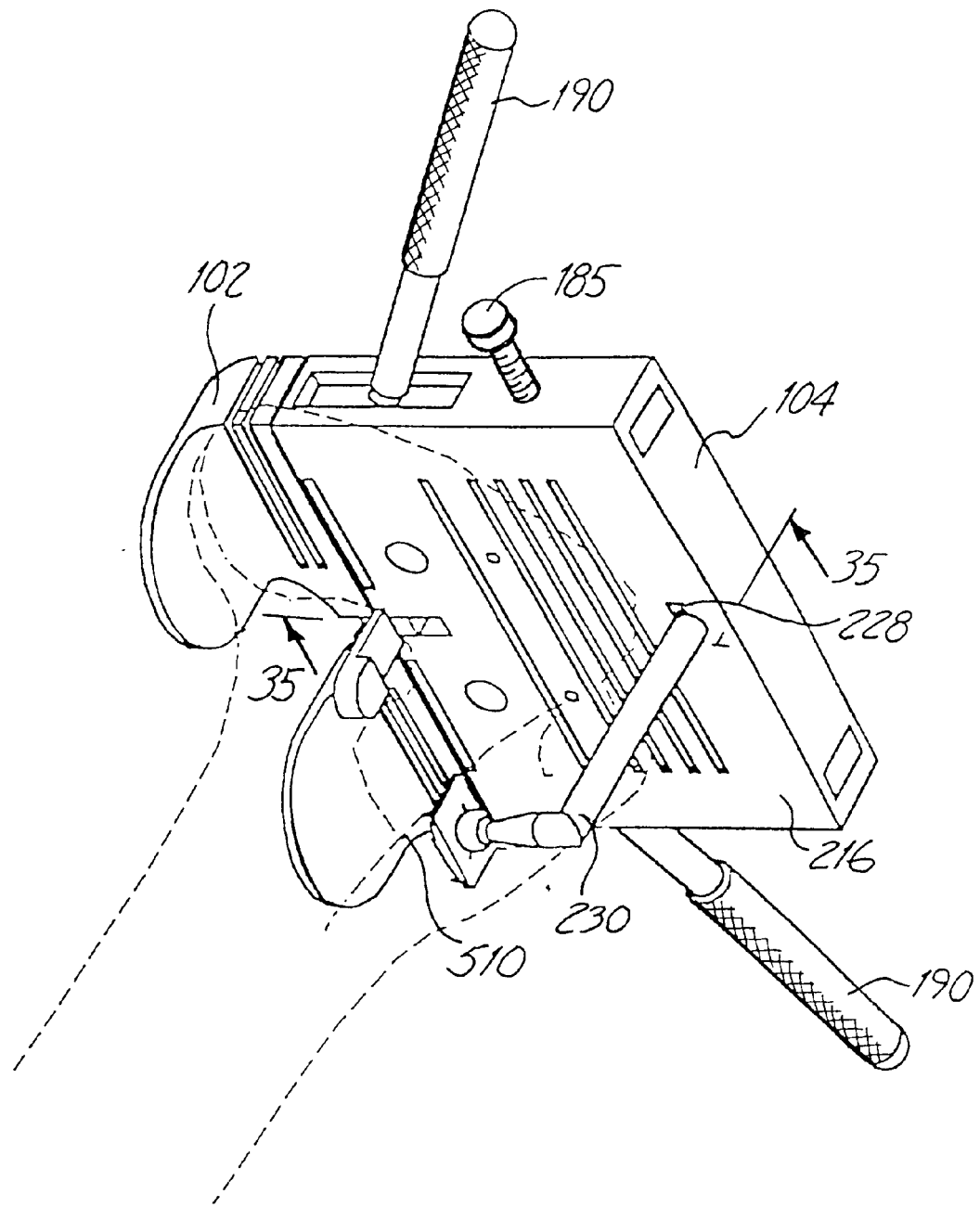
FIG. 34 is perspective view of the femoral resection instrument in place on the femur (in phantom lines) being used to measure the proper size for the femoral prosthesis component.
Figure 35:
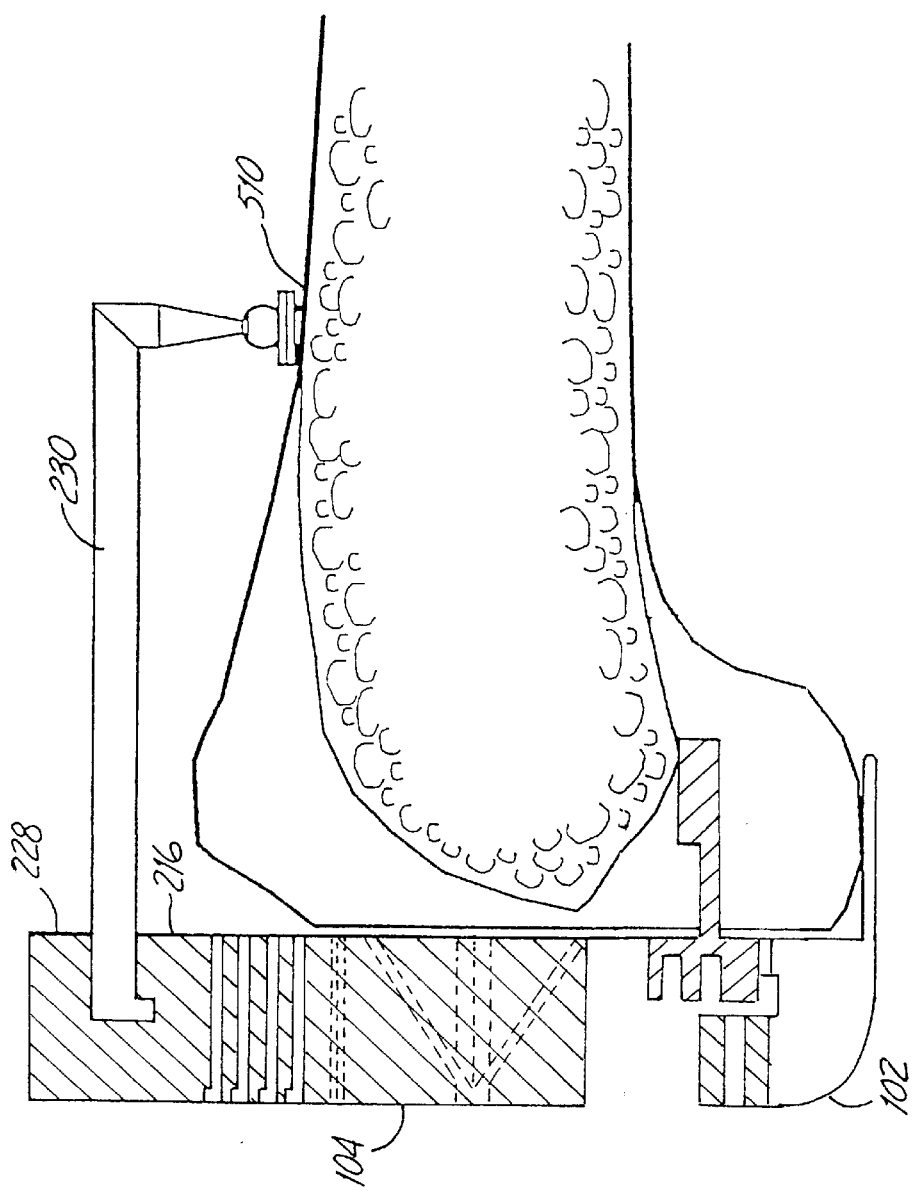
FIG. 35 is a sectional view along lines 35—35 of FIG. 34.
Figure 36:
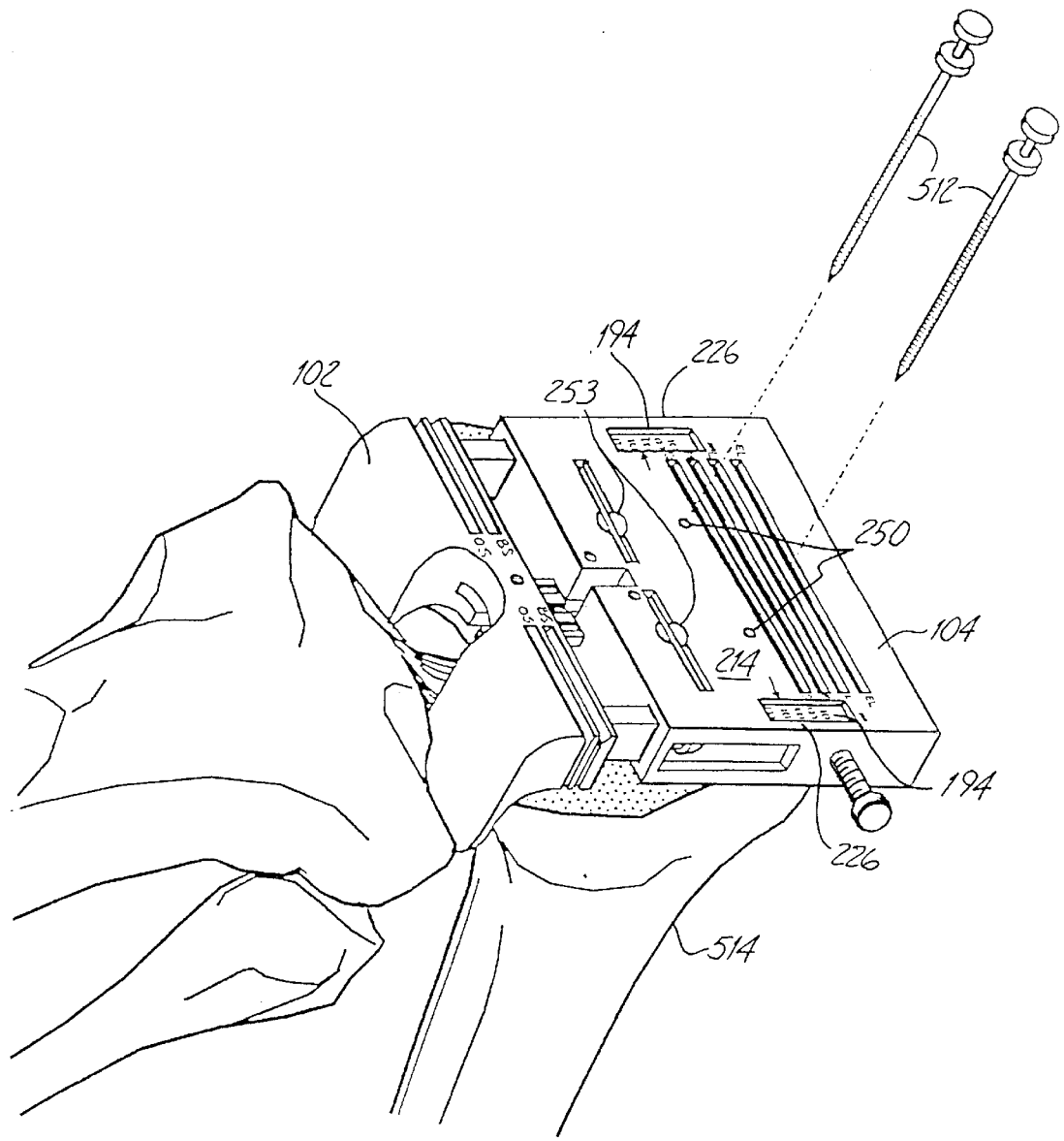
FIG. 36 is a perspective view of the femoral resection instrument on the distal end of a femur being used to determine the size of the femoral prosthesis component.

Once the femoral resection guide 100 is properly aligned, the size of the femoral prosthesis component is determined. FIGS. 34 and 35 show how, in this step, the anterior femoral target 230 is secured to the bottom surface 216 of anterior body portion 104 at anterior key holder 228. Screws 185 are pulled to remove tip 191 from either holes 184, 186 so that the anterior body portion 104 can slide relative to posterior body portion 102. Anterior body portion 104 is positioned relative to posterior body portion 102 at the point where anterior femoral target 230 contacts the side of the anterior femoral cortex proximate shallow groove 510. As shown in FIG. 36, the size of the femoral prosthesis component is then obtained from the markings 194 that are read through windows 226 on the top surface 214 of the anterior body portion 104. For example, the markings may use codes for various sizes of recommended components, such as "S" for small, "M" for medium, "L" for large, "EL" for extra large, or similar means for designating the measured size. These window readouts then guide the surgeon in the proper selection of cutting guides 218, which are similarly marked. Corresponding marking concepts are used for designating the recommended posterior cutting guides 112 and 114 or 116 and 118. For example, according to the window readout, the surgeon would select either the "BETWEEN SIZE" or the "ON SIZE" pair of guides for use, as shown in FIGS. 36 and 37. The particular scale between markings may vary according to the geometries of the component system. In one system, the spacing is about 4 millimeters between sizes. Handles 190, shown in FIG. 1, can be used to stabilize the femoral resection guide 100 during this sizing process.

Once the size of the femoral prosthesis component is determined, the anterior femoral target 230 is removed or rotated to the side. Then, the anterior body portion 104 is secured with respect to the posterior body portion 102 using the spring screws 185. The screws 185 are placed with tips 191 in the near holes 184 if the measurement of the size of the femoral bone was close to one of the standard sizes of the femoral prosthesis components. The screws 185 are placed with tips 191 in the far holes 186 if the measurement of the size of the femoral bone is between available sizes of the femoral prosthesis components. The selection of which set of holes 184, 186 to use is a judgment of the surgeon.

With the posterior body portion 102 and the anterior body portion 104 secured to each other, pins 512 can be passed through holes 250 into the femur 514, as illustrated in FIGS. 36 and 38. Holes are drilled into the distal femur 514 using holes 253 as a guide. These bone holes will eventually receive the posts of the femoral prosthesis component. The femoral resection guide 100 is then ready for the surgeon to perform the cuts on the distal end of the femur 514. Rather than using pins 512 within holes 250 to secure the femoral resection guide 100, pins of larger diameter could be placed within drill holes 253 and associated holes in the bones, and could also be used to secure the resection guide 100 during the cutting process. Holes 250 can also be located at various locations on the instrument, and may have axes or surfaces oriented at other than 90° to the top surface of the instrument.

If the near prong holes 184 were used to secure the anterior body portion 104, i.e., the bone size matches one of the component sizes (i.e., "ON SIZE" or "OS"), the near posterior cutting guides 112, 114 should be used to perform the cuts to the posterior femoral condyles 516. If the far prong holes 186 were used to secure the anterior body portion 104, i.e., bone size is between available component sizes (i.e., "BETWEEN SIZE" or "BS"), then the far posterior cutting guides 116, 118 should be used to cut the posterior femoral condyles 516, as shown in FIG. 37. Standard cutting tools can be used.

Figure 39:
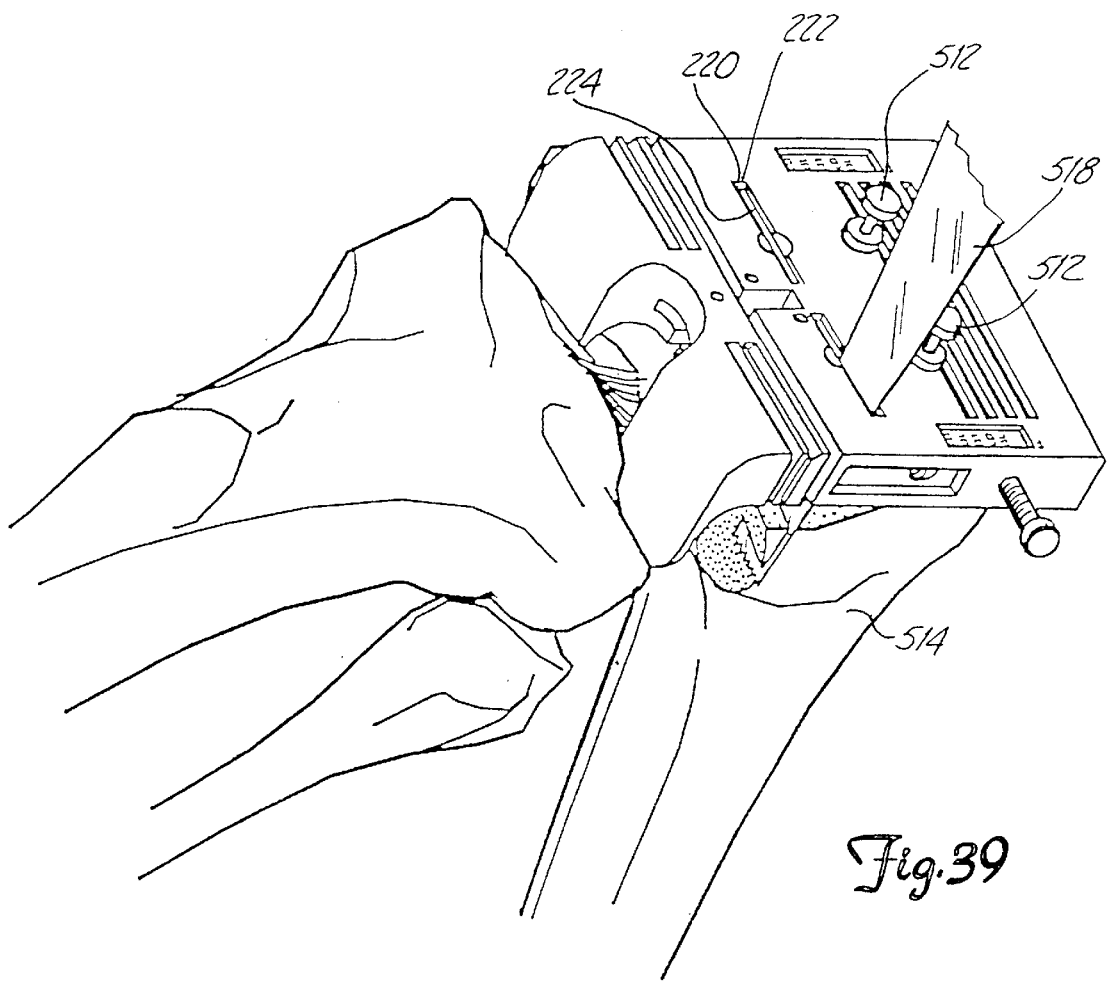
FIG. 39 a perspective view of the femoral resection instrument on the distal end of a femur being used to make a posterior chamfer cut.

To perform the anterior femoral cuts, the selected size of the femoral prosthesis component is used to select the corresponding cutting guide 218. A bone cutter 518 is inserted into the proper cutting guide 218. The cutter 518 is used to perform the cut of the anterior of the femur 520, as shown in FIG. 38. If the bone size falls between two available sizes of the femoral component, the anterior cut is made through the anterior cutting guide corresponding to the smallest of the two component sizes. Similarly, the chamfer cutting guides 220, 222 are used to perform the posterior and anterior chamfer cuts to the femur, as shown in FIGS. 39. The cuts to the distal end of the femur can be performed in any order, although there is some convenience in performing the anterior and posterior cuts before the chamfer cuts. Drill holes 253 can be used to drill the appropriate holes basically at any time the anterior body portion 104 is properly located, although if pins are to be used within holes 250, there is some advantage to drilling the holes in the femur with the resection guide secured.

Stated another way, if the far prong holes are used due to the size of the patient, then it is recommended to adjust to the next smallest size for cutting guide selection. However, if the near prong holes are used, then it is recommended to select the larger of the two sizes in the size range.

Various specific embodiments are described, which are intended to be illustrative rather than limiting. Certain specific embodiments are related to the small, medium, large and extra large femoral components of an implant system known under the trade name of Genesis, sold by Smith-Nephew Richards, Inc. The number of cutting guides, and the distances and/or orientations between them, would likely differ with other implant systems having different femoral component geometries.

We claim:

1. An instrument for distal femur cutting and prosthesis measuring, comprising:

a first portion defining a first surface for contacting the distal end of a femur and having:

a first plurality of cutting slots spaced from each other along and extending through the first distal femur contact surface with the slots being aligned generally perpendicular to the first distal femur contact surface;

at least two angled cutting slots aligned at an angle of less than 90° relative to a plane defined by the first plurality of cutting slots with the angled cutting slots extending through the first contact surface at spaced locations from each other and converging at a common point at a side of the first portion opposite the first contact surface, wherein the first plurality of cutting slots are all located on the first portion together relative to the location of the angled cutting slots on the first portion; and a second portion further defining the first contact surface and having a second surface for contacting at least one of a pair of posterior femoral condyles, and having at least one prong extending generally perpendicular to the second surface, the prong being slidably moveable within and relative to the first portion along an axis generally parallel to the first contact surface so that the second contact surface is maintained generally perpendicular relative to the first contact surface, the second portion further having at least one third cutting slot aligned generally perpendicular to the first contact surface.

2. The instrument of claim 1 and further comprising:

means for selectively fixing the prong of the second portion relative to the first portion at one of a set of first predetermined locations along the prong.

3. The instrument of claim 2 and further comprising:

means for selectively fixing the prong of the second portion relative to the first portion at locations along the prong intermediate to the first predetermined locations.

4. The instrument of claim 1 and further comprising:

an elongate pin for contacting the intramedullary groove being slidably disposed in the first portion for sliding movement relative to and in a direction generally perpendicular to the first femur contact surface.

5. The instrument of claim 1 wherein the second distal contact surface includes a first portion for contacting a first femoral posterior condyle and a second portion for contacting a second femoral posterior condyle with the second portion spaced from the first portion along a lateral axis.

6. The instrument of claim 1 wherein the first plurality of cutting slots includes at least four slots wherein the relative spacing between each slot of the first plurality of slots and the third cutting slot corresponds to the sizing of one of a plurality of presized femur prostheses for mounting on the distal end of the femur.

7. The instrument of claim 1 wherein the third cutting slot comprises two slots laterally spaced from each other along the first contact surface.

8. A method of shaping a distal end of femur with an instrument, the method comprising:

positioning a first surface of the instrument in contact with a distal end of a femur;

positioning a second surface of the instrument in contact with at least one femoral posterior condyle, the second surface being generally perpendicular to the first surface;

selectively fixing the spacing between the second surface and one of a plurality of predetermined reference points on the first surface, wherein the spacing between each of the predetermined reference points and the second surface corresponds to the sizing of one of a plurality of presized femur prostheses for mounting on the distal end of the femur;

cutting an anterior portion of the distal end of the femur through one of a first plurality of cutting slots extending through and generally perpendicular to the first surface;

cutting a posterior portion of the distal femur through at least one cutting slot extending through and generally perpendicular to the first surface; and making chamfered cuts in a distal portion of the distal femur with at least one of a plurality of angled cutting slots extending through the instrument at angles of less than 90° relative to the first contact surface and converging at a side of the instrument opposite the first contact surface, wherein the first plurality of cutting slots are all located on the first surface together relative to the location of the angled cutting slots on the first surface.

9. An instrument for distal femur cutting and prosthesis measuring, comprising:

a first portion defining a first surface for contacting the distal end of a femur and a second portion further defining the first contact surface and having a second surface for contacting at least one of a pair of posterior femoral condyles;

at least one first cutting slot extending through and being generally perpendicular to the first distal femur contact surface and being located on at least one of the first portion and the second portion;

at least two angled cutting slots aligned at an angle of less than 90° relative to a plane defined by the first cutting slots with the angled cutting slots extending through the first contact surface at spaced locations from each other and converging at a common point at a side of the first portion opposite the first contact surface;

at least one second cutting slot extending through and generally perpendicular to the first contact surface and being located on at least one of the first portion and the second portion;

wherein the two angled cutting slots are disposed between the first cutting slot and the second cutting slots; and means for selectively fixing spacing between the first cutting slot and the second cutting slot so that the spacing between the first and second cutting slots corresponds to the sizing of one of a plurality of presized femur prostheses for mounting on the distal end of the femur.

10. An instrument for distal femur cutting and prosthesis measuring, comprising:

a first surface for contacting the distal end of a femur and a second surface for contacting at least one of a pair of posterior femoral condyles;

a first plurality of cutting slots extending through and being generally perpendicular to the first contact surface;

at least two angled cutting slots aligned at an angle of less than 90° relative to a plane defined by the first cutting slots with the angled cutting slots extending through the first contact surface at spaced locations from each other and converging at a common point at a side of the first portion opposite the first contact surface; and at least one second cutting slot extending through and generally perpendicular to the first contact surface, the second cutting slot being located nearer the second contact surface than the first plurality of cutting slots, wherein the two angled cutting slots are disposed between the locations of the first cutting slots and the second cutting slots, wherein the first plurality of cutting slots are all located together on a portion of the first contact surface relative to the location of the angled cutting slots on the first contact surface, and wherein the spacing between one of the first cutting slots and the second cutting slot corresponds to the sizing of one of a plurality of presized femur prostheses for mounting on the distal end of the femur.

* * * * *